United States Patent
Andersson

(10) Patent No.: US 10,179,032 B2
(45) Date of Patent: *Jan. 15, 2019

(54) METHOD AND SYSTEM FOR COMPUTER ASSISTED SURGERY

(71) Applicant: Ortoma AB, Gothenburg (SE)

(72) Inventor: Matts Andersson, Lerum (SE)

(73) Assignee: Ortoma AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/004,887

(22) Filed: Jun. 11, 2018

(65) Prior Publication Data

US 2018/0289433 A1    Oct. 11, 2018

Related U.S. Application Data

(62) Division of application No. 14/419,515, filed as application No. PCT/SE2013/050952 on Aug. 5, 2013, now Pat. No. 9,993,305.

(30) Foreign Application Priority Data

Aug. 8, 2012   (SE) ...................................... 1250919

(51) Int. Cl.
  *A61B 17/34*   (2006.01)
  *A61B 34/20*   (2016.01)
  (Continued)

(52) U.S. Cl.
  CPC .......... *A61B 34/20* (2016.02); *A61B 17/1757* (2013.01); *A61B 34/10* (2016.02);
  (Continued)

(58) Field of Classification Search
  CPC ... A61B 34/10; A61B 34/20; A61B 2034/101; A61B 2034/102; A61B 2034/105;
  (Continued)

(56) References Cited

U.S. PATENT DOCUMENTS

| 5,440,392 A | 8/1995 | Pettersen et al. |
| 6,166,809 A | 12/2000 | Pettersen et al. |

(Continued)

FOREIGN PATENT DOCUMENTS

| WO | 199116598 A1 | 10/1991 |
| WO | 199611624 | 4/1996 |

(Continued)

OTHER PUBLICATIONS

Amendment and Response to Election/Restriction Requirement dated Oct. 30, 2017, in connection with U.S. Appl. No. 14/419,515, filed Feb. 4, 2015.

(Continued)

*Primary Examiner* — Eric S Gibson
(74) *Attorney, Agent, or Firm* — Downs Rachlin Martin PLLC

(57) ABSTRACT

A method and system for computer assisted orthopedic feedback of at least one surgical object relative a pre-operative plan are disclosed. The pre-operative plan includes a virtual object, which is the virtual representation of the surgical object, and a virtual structure, which is the virtual representation of the patient structure. The method comprises providing the pre-operative plan including planned position and orientation of the virtual object relative to of the virtual structure; obtaining the position of the patient structure based on a surface of the patient structure using a surgical navigation system; obtaining the position of the surgical object using the surgical navigation system; registering the patient structure to the virtual structure and the surgical object to the virtual object; tracking a current position and orientation of the surgical object using the surgical navigation system; and providing feedback of a current position and orientation of the surgical object relative to the planned position and orientation of the virtual (Continued)

object based on the tracked current position and orientation of the surgical object.

16 Claims, 11 Drawing Sheets

(51) Int. Cl.
 *A61B 34/10* (2016.01)
 *A61B 17/17* (2006.01)
 *A61B 17/16* (2006.01)
 *A61B 17/00* (2006.01)
 *A61B 90/00* (2016.01)

(52) U.S. Cl.
 CPC . *A61B 17/1622* (2013.01); *A61B 2017/00725* (2013.01); *A61B 2034/102* (2016.02); *A61B 2034/105* (2016.02); *A61B 2034/107* (2016.02); *A61B 2034/2048* (2016.02); *A61B 2034/2055* (2016.02); *A61B 2034/2068* (2016.02); *A61B 2090/364* (2016.02)

(58) Field of Classification Search
 CPC ........ A61B 2034/107; A61B 2034/108; A61B 2034/2046; A61B 2034/2048; A61B 2034/2055; A61B 2034/2057; A61B 2034/2063; A61B 2034/2065; A61B 2034/2068; A61B 2034/2072; A61B 17/17; A61B 17/1703; A61B 17/1707
 See application file for complete search history.

(56) References Cited

U.S. PATENT DOCUMENTS

| | | | | |
|---|---|---|---|---|
| 8,768,437 | B2* | 7/2014 | Barrick | A61B 5/064 |
| | | | | 378/205 |
| 8,974,468 | B2* | 3/2015 | Borja | A61F 2/4657 |
| | | | | 606/102 |
| 9,192,459 | B2* | 11/2015 | Bonutti | A61B 17/025 |
| 9,585,597 | B2* | 3/2017 | McCaulley | A61B 5/06 |
| 9,603,665 | B2* | 3/2017 | Bowling | A61B 17/16 |
| 9,636,185 | B2* | 5/2017 | Quaid | G06F 19/00 |
| 9,707,043 | B2* | 7/2017 | Bozung | A61B 17/32002 |
| 9,713,506 | B2* | 7/2017 | Fanson | A61B 46/10 |
| 9,993,305 | B2* | 6/2018 | Andersson | A61B 34/20 |
| 2004/0044295 | A1* | 3/2004 | Reinert | A61B 34/20 |
| | | | | 600/587 |
| 2004/0152972 | A1* | 8/2004 | Hunter | A61B 17/025 |
| | | | | 600/424 |
| 2006/0142657 | A1* | 6/2006 | Quaid | G06F 19/00 |
| | | | | 600/424 |
| 2007/0238981 | A1* | 10/2007 | Zhu | A61B 90/36 |
| | | | | 600/424 |
| 2007/0249967 | A1* | 10/2007 | Buly | A61B 5/1121 |
| | | | | 600/595 |
| 2008/0195109 | A1* | 8/2008 | Hunter | A61B 17/155 |
| | | | | 606/87 |
| 2009/0234217 | A1* | 9/2009 | Mire | G16H 50/50 |
| | | | | 600/407 |
| 2010/0030063 | A1* | 2/2010 | Lee | A61B 5/06 |
| | | | | 600/424 |
| 2011/0251607 | A1 | 10/2011 | Kruecker et al. | |
| 2011/0275957 | A1 | 11/2011 | Bhandari | |
| 2013/0060146 | A1* | 3/2013 | Yang | A61B 5/055 |
| | | | | 600/476 |
| 2013/0060278 | A1* | 3/2013 | Bozung | A61B 17/32002 |
| | | | | 606/205 |
| 2013/0172907 | A1* | 7/2013 | Harris | A61B 34/20 |
| | | | | 606/130 |
| 2014/0193053 | A1* | 7/2014 | Kadoury | G06T 11/008 |
| | | | | 382/131 |
| 2014/0276943 | A1* | 9/2014 | Bowling | A61B 17/16 |
| | | | | 606/130 |
| 2014/0364858 | A1* | 12/2014 | Li | A61F 2/4609 |
| | | | | 606/91 |
| 2015/0157416 | A1* | 6/2015 | Andersson | A61B 34/10 |
| | | | | 606/102 |
| 2016/0022374 | A1* | 1/2016 | Haider | A61B 17/17 |
| | | | | 606/96 |
| 2016/0220385 | A1* | 8/2016 | Falardeau | A61F 2/4609 |
| 2017/0119475 | A1* | 5/2017 | McCabe | A61B 34/20 |
| 2017/0143433 | A1* | 5/2017 | Fanson | A61B 46/10 |
| 2017/0231709 | A1* | 8/2017 | Gupta | A61B 34/20 |
| | | | | 600/424 |

FOREIGN PATENT DOCUMENTS

| | | |
|---|---|---|
| WO | 2011134083 A1 | 11/2011 |
| WO | 2014025305 A1 | 2/2014 |

OTHER PUBLICATIONS

Non-Final Office Action dated Jan. 5, 2018, in connection with U.S. Appl. No. 14/419,515, filed Feb. 4, 2015.
Amendment and Response to Non-Final Office Action dated Mar. 1, 2018, in connection with U.S. Appl. No. 14/419,515, filed Feb. 4, 2015.
Notice of Allowance dated May 1, 2018, in connection with U.S. Appl. No. 14/419,515, filed Feb. 4, 2015.
Global Positioning Systems, Inertial Navigation, and Integration, Mohinder S. Grewal, Lawrence R. Weill, Angus P. Andrews, copyright 5 2001 John Wiley & Sons, Inc. PrintISBN0-471-35032-X Electronic ISBN0-471-20071-9, Appendix C—Coordinate Transformations.

* cited by examiner

METHOD AND SYSTEM FOR COMPUTER ASSISTED SURGERY

FIELD OF THE INVENTION

This invention pertains in general to the field of tracking movement of a surgical object. More particularly, the invention relates to tracking the position of the surgical object relative a planned position of the surgical object within a pre-operative plan. Feedback is provided of the position and orientation of the surgical object relative to a virtual representation thereof in the pre-operative plan. Any deviation between the two may be indicated to the surgeon.

BACKGROUND OF THE INVENTION

Various Computer Assisted Orthopedic Systems (CAOS) tools exist, which range from active robotic to passive or navigation systems. Active robotic systems are capable of performing surgery autonomously without interaction of the surgeon. Many times, the surgeon wants to be in control of the surgery, wherein the passive or navigation systems are preferred, which provide additional information during a procedure compared to conventional surgery but do not perform the surgical action. The surgeon controls the intervention but acts on additional patient information obtained from a pre-operative scan.

For an orthopedic intervention using a CAOS system, a pre-operative plan may or may not precede the actual surgery. One such system is the development of a surgical template, also referred to as a surgical guide, to be used during surgery to guide the surgical tools. The pre-operative plan may aid the surgeon to take decisions about the surgery before it commences. The pre-operative plan may be based on a three-dimensional scan of the patient, such as a CT or MRI scan. During planning, the surgeon will have access to the internal structures of the patient to plan the surgery, for example by volumetric scan data that can be displayed slice by slice, from various angles, etc. Planned paths of instruments relative to patient data are transferred to the surgical template. During surgery, the surgical template guides the path of the instrument. Hence, the system offers little flexibility for the surgeon to deviate from the planned path should that be necessary during the surgery. However, this is one way of physically integrating the pre-operative plan with the actual surgery. A benefit of the system is that the physical components do not need to be calibrated before surgery commences.

Robotic surgery is another possibility to carry out a pre-operatively plan. During the surgery, the surgical instrument is not in the hands of the surgeon but carried by a robot, which is only indirectly controlled by the surgeon. Since the physical components such as a camera and a robotic arm, are provided as an integrated unit, calibration between the components is not necessary. Therefore, these systems are not only costly, but their flexibility is limited by the degrees of freedom and limited feedback to the surgeon to take corrective actions.

Common to robotic surgical systems is that they use a navigation system to guide the robot. Such navigation systems can comprise three major components: the surgical aspect, the virtual aspect, and the navigator. The surgical aspect is the bones and accompanying tissues in the surgical field. The virtual aspect is the virtual representation of the surgical aspect. Finally, the navigator establishes a coordinate system in which the location and orientation of the target as well as "end-effectors" are expressed. The "end-effectors" can be surgical instruments or active devices used during surgery.

Three major procedural requirements are essential to successful navigation. First, end-effectors must be calibrated for correct representation of their shapes and geometry in the coordinate system established by the navigator. Second, "registration" establishes correspondence between the surgical and the virtual aspect. Finally, "dynamic referencing" using dynamic reference bases establishes a local coordinate system that compensates for possible motion of the navigator or the surgical aspect during surgical action.

Examples of robotic surgical systems are the RoboDoc surgical system, the Acrobot system, and the CASPAR system. Common to them is that they use pre-operative and intra-operative data obtained through computer navigation to control the performance of the robot. In these systems, the surgical aspect is registered in the coordinate system of the robot to provide correspondence between the virtual and the surgical aspect, and the actions of the robot is controlled by the virtually planned path or movements of virtual end-effectors. The position of the robotic arm is known in its coordinate system. This makes it possible to also have a fixed relationship between the coordinate system of the robot and the coordinate system of the plan for the surgery, and further calibration is not required.

Patient anatomical landmarks can be identified by cameras while the patient is positioned within reach of the robotic arm. In the pre-operative plan, the same anatomical landmarks are present. The pre-operative plan contains planned movement of end-effectors relative the anatomical landmarks. During surgery, the same anatomical landmarks are identified and movement of the robot can be controlled in relation thereto based on the plan data to position orthopedic implants. The surgery is restricted by the operating range of the robot. The pre-operative plan may be implemented by the robot, whereby the end-effectors are completely controlled by the plan data, such as in the RoboDoc system. Alternatively, the plan data can be used to apply active constraints, as in the Acrobot system, such that the surgeon is assisted to achieve accurate cuts and paths while ensuring the pre-operative plan is followed. Common to these systems is that the surgeon is more or less restricted by the robotic system, and is not fully free to make his own choices during surgery.

Attempts to use Stereotactic surgery for surgical interventions have ben made. However, the difficulty to obtain a reliable bone reference has limited this type of surgery to brain surgery. Before scanning the patient, a frame is attached to the scull of the patient. The frame is used as a fiduciary marker to register the patient to the scan data during the surgery, and to track the position of a surgical instrument to the reference frame, and, thus, to the patient data. During the surgery, the tip of a probe can be tracked and related to the patient scan data. However, systems using artificial landmarks that are present during scanning, such as CT and/or MRI scanning, as well as during surgery for registering patient scan data to patient data are not useful for orthopedic surgery. An example of such as system is for example described in WO 96/11624. During the surgery, these systems relate patient scan or segmented data, such as in the form a 3D representation of the scan data, to the tracked position of the surgical instrument to provide additional information to the surgeon, such as intraoperative measurement tool and tracking of tools with respect to bony anatomy displayed on the screen, and act on information in a timely manner. However, the purpose of these systems is to provide information about anatomical structures that otherwise would not be visible to the surgeon, but do not give any guidance. Recently, attempts have been made to rely on anatomical landmarks rather than artificial landmarks for the registration of the patient's image data set to the position of the instrument. However, these systems are still limited to displaying the patient image data relative to the position of the surgical instrument. Also, the data displayed are intrinsic to the patient scan data, and do not relate to the planning of an implant.

Orthopaedic surgery MIS (Minimally Invasive Surgery) procedures have been proposed for the planning of orthopedic implant surgeries. Such systems do not rely on volumetric patient image data. Instead, these systems are image free and use information gathered intra-operatively—such as centers of rotation of the hip, knee, and ankle and visual information like anatomical landmarks—from which desired positions of the implants are calculated. These systems provide no planning capabilities before the surgery and navigation is based on the information that is calculated rather than obtained from the patient's true anatomy. Structures shown on a screen are always approximations, such as 3D models obtained from a library of bones structures based on the calculations made. Hence, such are less precise compared to image based orthopedic navigation systems. Furthermore, these systems do not provide any pre-operative planning possibilities, since the calculations and simulations are made intra-operatively. Furthermore, surgical tools are not tracked during the surgical action. Such system is for example disclosed in US application No. 2011/0275957.

WO2011134083 discloses systems and methods for surgical guidance and image registration, in which three-dimensional image data associated with an object or patient, is registered to topological image data obtained using a surface topology imaging device. The surface topology imaging device may include fiducial markers, which may be tracked by an optical position measurement system that also tracks fiducial markers on a movable instrument. The instrument may be registered to the topological image data, such that the topological image data and the movable instrument are registered to the three-dimensional image data. The system may also co-register images pertaining to a surgical plan with the three-dimensional image data. The fiducial markers may be tracked according to surface texture. The system utilizes fiducial markers attached to surgical instruments that have a fixed relationship relative to an end-effector thereof. Hence, the system becomes complicated and expensive, since special-purpose surgical instruments having the fiducial markers have to be used with the system. The position of the end-effector of the surgical tool is determined and recorded using a 3D model of the surgical tool, which is imported from computer aided design (CAD) drawings, in which the tool tip is known. Alternatively, the surgical tool can be profiled with a structured light scanner to obtain its 3D geometry. The tool tip and orientation axis are determined from an acquired point cloud. These are time-consuming processes for obtaining the positions of the tool tip relative the fiducial markers, which is undesired during surgical action where time is a scarce resource, not only during the surgical action itself but also in preparation therefore.

US2009234217A1, US2011251607, and US2007238981A1 disclose various aspects of navigation systems. However, utilizing various types of fiducial markers, they all suffer from at least the same issues as the navigation system disclosed in WO2011134083, such as in relation to the calibration of the position of the end-effector or tool-tip.

Hence, an improved surgical navigation method and system and associated surgical instruments would be advantageous, and in particular allowing for improved guidance, precision, increased flexibility, cost-effectiveness, robustness, reliability, efficiency and/or patient safety would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing flexible orthopedic surgical guidance integrated with an image-based pre-operative plan according to the appended patent claims.

According to a first aspect, a method for computer assisted orthopedic feedback of at least one surgical object relative a pre-operative plan, wherein the surgical object is moveable relative to a patient structure during surgery is provided. The pre-operative plan includes a virtual object, which is the virtual representation of the surgical object, and a virtual structure, which is the virtual representation of the patient structure. The method comprises providing the pre-operative plan including planned position and orientation of the virtual object relative to of the virtual structure; obtaining the position of the patient structure based on a surface of the patient structure using a surgical navigation system; obtaining the position of the surgical object using the surgical navigation system; registering the patient structure to the virtual structure, and optionally or additionally registering the surgical object to the virtual object; tracking a current position and orientation of the surgical object using the surgical navigation system; and providing feedback of a current position and orientation of the surgical object relative to the planned position and orientation of the virtual object based on the tracked current position and orientation of the surgical object.

Tracking the current position and orientation of the surgical object may comprise calibrating the position of an end-effector of the surgical object relative a calibration unit within the surgical navigation system.

Calibrating the position of the end-effector of the surgical object may comprise calibrating the position of a navigation unit of the surgical object relative a surface with a predetermined position of the calibration unit.

Calibrating the position of the navigation unit of the surgical object may comprise determining the position of a navigation unit of the calibration unit, the navigation unit having a fixed positional relationship relative the surface with a predetermined position. Optionally or additionally calibrating the position of the navigation unit of the surgical object may comprise registering multiple positions of the navigation unit of the surgical object while it is moved in at least one plane and the position of the end-effector is substantially fixed at the surface with the predetermined position, and determining the position of the end-effector based on the registered multiple positions of the navigation unit of the surgical object.

Providing the feedback may comprise proving at least one of: visual feedback of current position and orientation of the virtual object relative to the planned orientation and position of the virtual object on a display in response to the tracked current position and orientation of the surgical object; visual indication of the deviation of a current position and orientation of the virtual object relative the planned position and orientation of the virtual object on a display in response to the tracked current position and orientation of the surgical object; and visual indication of the deviation of the current position and orientation of the surgical object relative the planned position and orientation of the virtual object in response to the tracked current position and orientation of the surgical object, wherein the visual indication is indicated at the surgical object.

The method may comprise tracking the current position and orientation of the patient structure, and compensating the position and orientation of the virtual object based on the tracked current position and orientation of the patient structure.

Obtaining the position of the surgical object may comprise obtaining the position and orientation of at least one of a bony anatomy of the patient, a surgical template having at least one surface with a shape that is complementary to the shape of the bony anatomy of the patient, a surgical instrument, and an implant for implantation into the patient structure. Obtaining the position of the patient structure may comprise obtaining the position and orientation of a bony anatomy of the patient.

The method may comprise obtaining the position of the patient structure using a 3D-6D navigation system having a first accuracy. Additionally or alternatively, the method may comprise obtaining the position of the surgical object using a 6D navigation system having a second accuracy. The second accuracy may be equivalent or higher than the first accuracy.

Tracking the current position and orientation of the surgical object may comprise tracking using at least one gyro and at least one accelerometer to generate position and orientation data of the surgical object. The method may comprise wirelessly transferring the position and orientation data of the surgical object from the surgical navigation system to a position communication hub.

Tracking the current position and orientation of the patient structure may comprise tracking the position of a navigation unit, using the surgical navigation system, attached to the patient structure.

Providing the pre-operative plan may comprise: accessing volumetric scan data, wherein the scan data comprises patient structure scan data; converting the patient structure scan data into the virtual structure, which comprises a three dimensional representation of the patient structure; planning at least one position and orientation of the virtual object relative to the virtual structure; registering the planned position and orientation of the virtual object; and including at least one of the scan data and the three dimensional model of the virtual structure together with the planned position and orientation of the virtual object in the pre-operative plan.

According to a second aspect, a system for computer assisted orthopedic feedback of at least one surgical object relative a pre-operative plan is provided. The surgical object is moveable relative to a patient structure during surgery. The pre-operative plan includes a virtual object, which is the virtual representation of the surgical object, and a virtual structure, which is the virtual representation of the patient structure. The system comprises a position registration unit adapted to obtain at least one position of the patient structure based on a surface thereof and at least one position of the surgical object; a planning unit adapted to provide the pre-operative plan including planned position and orientation of the virtual object relative to the virtual structure, and to register the patient structure to the virtual structure, and optionally or additionally registering the surgical object to the virtual object; a tracking unit adapted to track a current position and orientation of the surgical object; a communication hub adapted to communicate position data from the position registration unit to the planning unit, and from the tracking unit to the planning unit; and a feedback device adapted to provide feedback of the current position and orientation of the surgical object relative to the planned position and orientation of the virtual object in response to the tracked current position and orientation of the surgical object.

The system may comprise a calibration unit for calibrating the position of an end-effector of the surgical object relative the calibration unit.

The calibration unit may comprise a surface having a predetermined position for receiving the end-effector of the surgical object, and optionally having a predetermined shape for positioning the end-effector in a substantially fixed position.

The calibration unit may comprise a navigation unit having a fixed positional relationship relative the surface with a predetermined position. Optionally or additionally the surface with a predetermined position has a shape to position the end-effector in at least one plane or position and to allow the surgical object to be freely moveable in at least one other plane. The position registration unit may be adapted to register multiple positions of the navigation unit of the surgical object as it is moved. The calibration unit may be adapted to determine the position of the end-effector based on registered multiple positions.

The feedback device may comprise an indicator, which may be integrated with the surgical object. The indicator may be adapted to provide indication of the deviation of the current position and orientation of the surgical object relative the planned position and orientation of the virtual object. The indicator may comprise a visual indicator, a tactile indicator, and/or an audio indicator.

The feedback device may comprise comprises at least one of: visual indicator adapted to provide, on a display, visual feedback of current position and orientation of the virtual object relative to the planned orientation and position of the virtual object in response to the tracked current position and orientation of the surgical object; visual indicator adapted to provide, on a display, visual indication of the deviation of the current position and orientation of the virtual object relative the planned position and orientation of the virtual object in response to the tracked current position and orientation of the surgical object; visual indicator, which is integrated with the surgical object and adapted to provide visual indication of the deviation of the current position and orientation of the surgical object relative the planned position and orientation of the virtual object.

The tracking unit may be adapted to track the current position and orientation of the patient structure. The tracking unit may additionally or alternatively be adapted to compensate the position and orientation of the virtual object based on the tracked current position and orientation of the patient structure.

The tracking unit may be adapted to track a surgical object in the form of at least one of a bony anatomy of the patient, a surgical template having at least one surface with a shape that is complementary to the shape of the bony anatomy of the patient, position and orientation of a surgical instrument relative to the patient structure, and an implant for implantation into the patient structure. The tracking unit may be adapted to track the patient structure in the form of a bony anatomy of the patient.

The tracking unit may comprise a navigation unit, such as position sensor, attachable to the patient structure at a fixed position relative the patient structure, and a tracking receiver, such as a position receiver, for receiving the position of the navigation unit.

The position registration unit may be adapted to obtain the position of the patient structure using a 3D-6D navigation system having a first accuracy, and additionally or alternatively to obtain the position of the surgical object using a 6D navigation system having a second accuracy. The second accuracy may be equivalent or higher than the first accuracy.

The tracking unit may comprise at least one gyro and at least one accelerometer to generate position and orientation data of the surgical object or an optical navigation system. The tracking unit may comprise a communication device adapted to wirelessly transferring the position and orientation data of the surgical object from the tracking unit to the position communication hub.

The planning unit may be adapted to: access volumetric scan data that comprises patient structure scan data; convert the patient structure scan data into the virtual structure, which comprises a three dimensional representation of the patient structure; generate, based on user interaction, a plan of at least one position and orientation of the virtual object relative to the virtual structure; register the planned position and orientation of the virtual object; and include at least one of the scan data and the three dimensional model of the virtual structure together with the planned position and orientation of the virtual object in the pre-operative plan.

According to a third aspect, a computer program product, executable on a programmable device contains instructions in the form of code segments, which when executed, performs the method according to embodiments of the invention.

According to a fourth aspect, a computer program product is stored on a computer usable medium, which comprises computer readable program means for causing a computer to carry out the various steps of embodiments of the method of the invention when executed.

Further embodiments of the invention are defined in the dependent claims.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
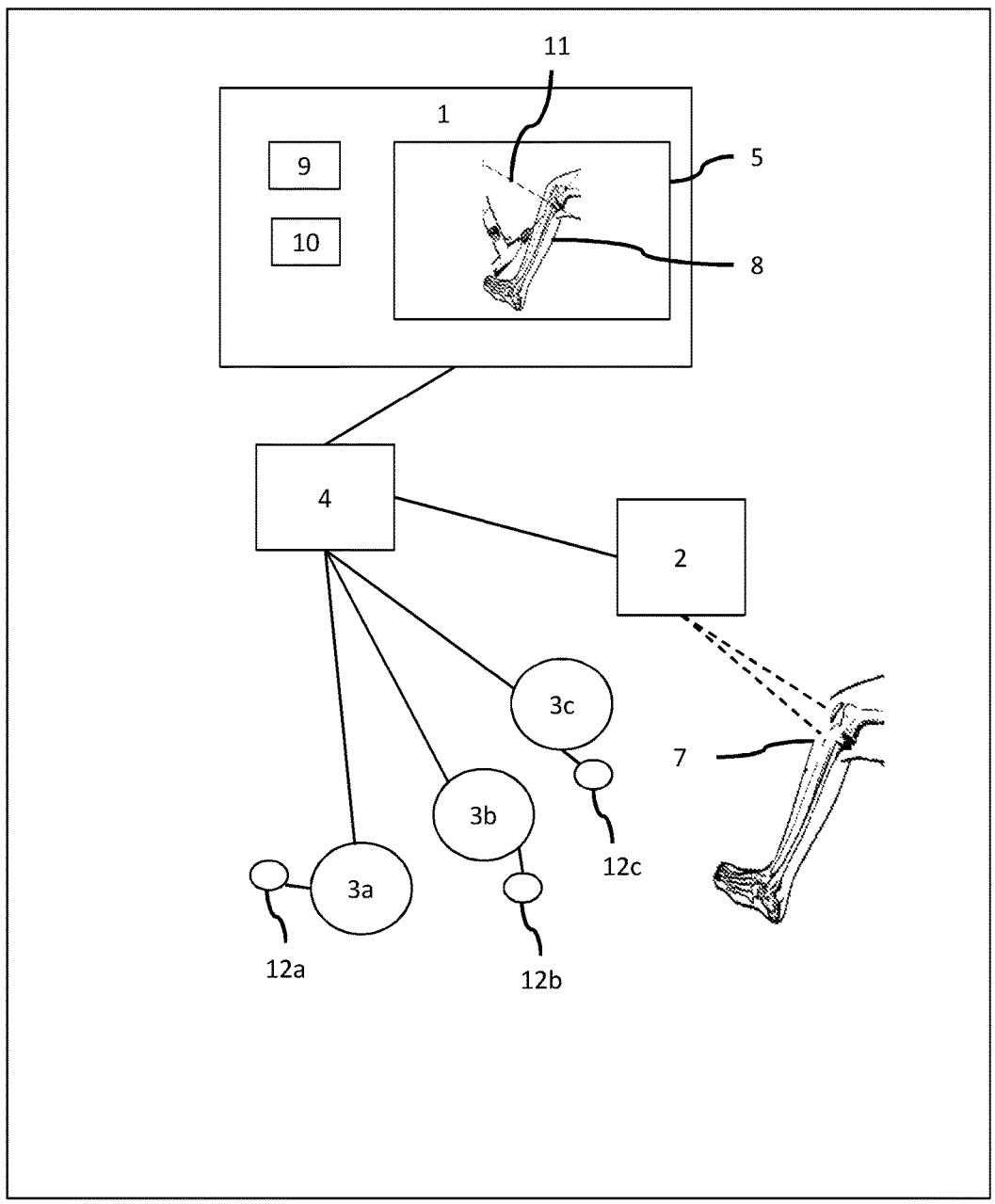
FIG. 1 is a schematic view of the system according to embodiments of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable for tracking the position of a surgical object during surgery, and transforming the position of the surgical object from the surgical theatre into a pre-operative plan of the surgical procedure. The pre-operative plan includes a virtual object, which is a virtual representation of the surgical object, and a virtual structure, which is a virtual representation of the patient structure, upon which the surgery is to be performed. Embodiments of the invention will be described with regard to orthopedic surgery. However, it will be appreciated that the invention is not limited to this application but may be applied to many other implant based surgical procedures, such as dentistry, dental surgery, etc., wherein the position of a surgical object, such as a drill or a dental implant, is tracked and transformed into the pre-operative plan. These planning procedures have in common that the pre-operative plan may comprise planning the position and orientation of an object that is extrinsic to the patient structure, such as a bony anatomy of the patient.

Embodiments of the invention are aimed at providing feedback of the current position and orientation of the surgical object relative the planned position and orientation of the virtual object during surgery in the context of the pre-operative plan. The feedback may be visualized on a display, wherein the virtual object and the virtual structure are rendered. During the course of the surgical procedure, the current or actual position and orientation of the virtual object relative to the position of the virtual structure will substantially correspond to the current position and orientation of the surgical object relative to the position of the patient structure. Hence, the actual position and orientation of the surgical object may be displayed relative to the pre-operative plan. Using embodiments of the invention, this may be done in real time. Thus, feedback is provided of the current or actual position and orientation of the virtual object relative to the planned position and orientation of the virtual object. Based on this feedback, the surgeon may be guided to the correct planned position of the surgical object. Yet, the surgeon can freely move the surgical object. Hence, embodiments of the invention provides guidance for correct positioning of the surgical object and is at the same time flexible since the ultimate decision of the position of the surgical object is in the hands of the surgeon. Also, feedback may be provided of the current or actual position and orientation of the virtual structure relative to the pre-operative plan of the virtual structure.

In embodiments of the invention, the position of the surgical object may be visually indicated, and plan data for the surgical object which e.g. may comprise a plurality of planned positions and/or orientations of a surgical instrument during various stages of the surgery. The virtual structure and the corresponding patient structure may be used as the common denominator in the pre-operative plan and in reality, respectively. A shape of the surface of the surgical object and/or the patient structure may be present in the pre-operative plan and during surgery. This shape can be used to provide the positional relationship of the patient structure in reality and the corresponding virtual structure in the pre-operative plan for the registration, as will be described below.

Figure 2:
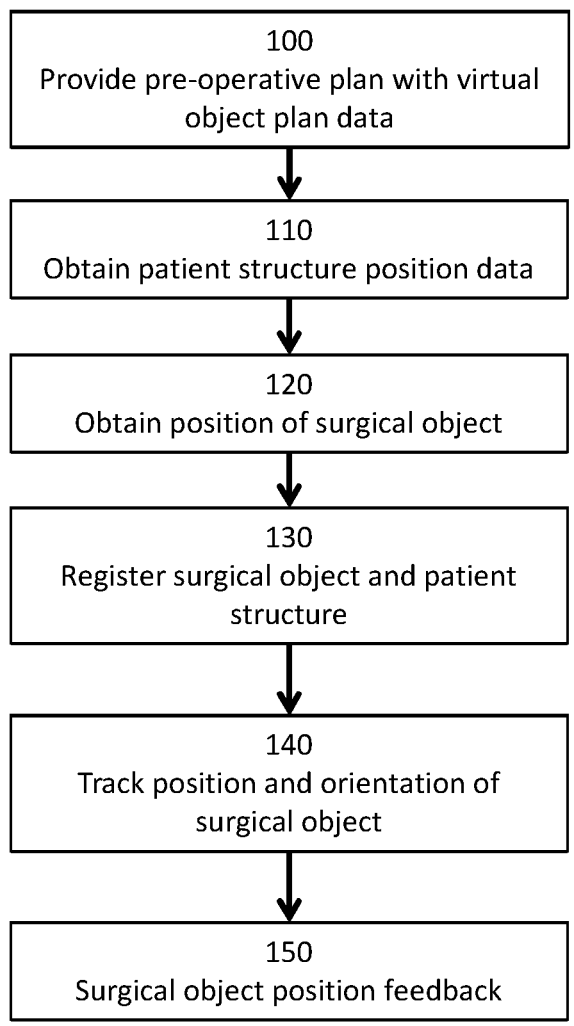
FIG. 2 is a flow chart of an embodiment for computer assisted orthopedic feedback.
Figure 6:
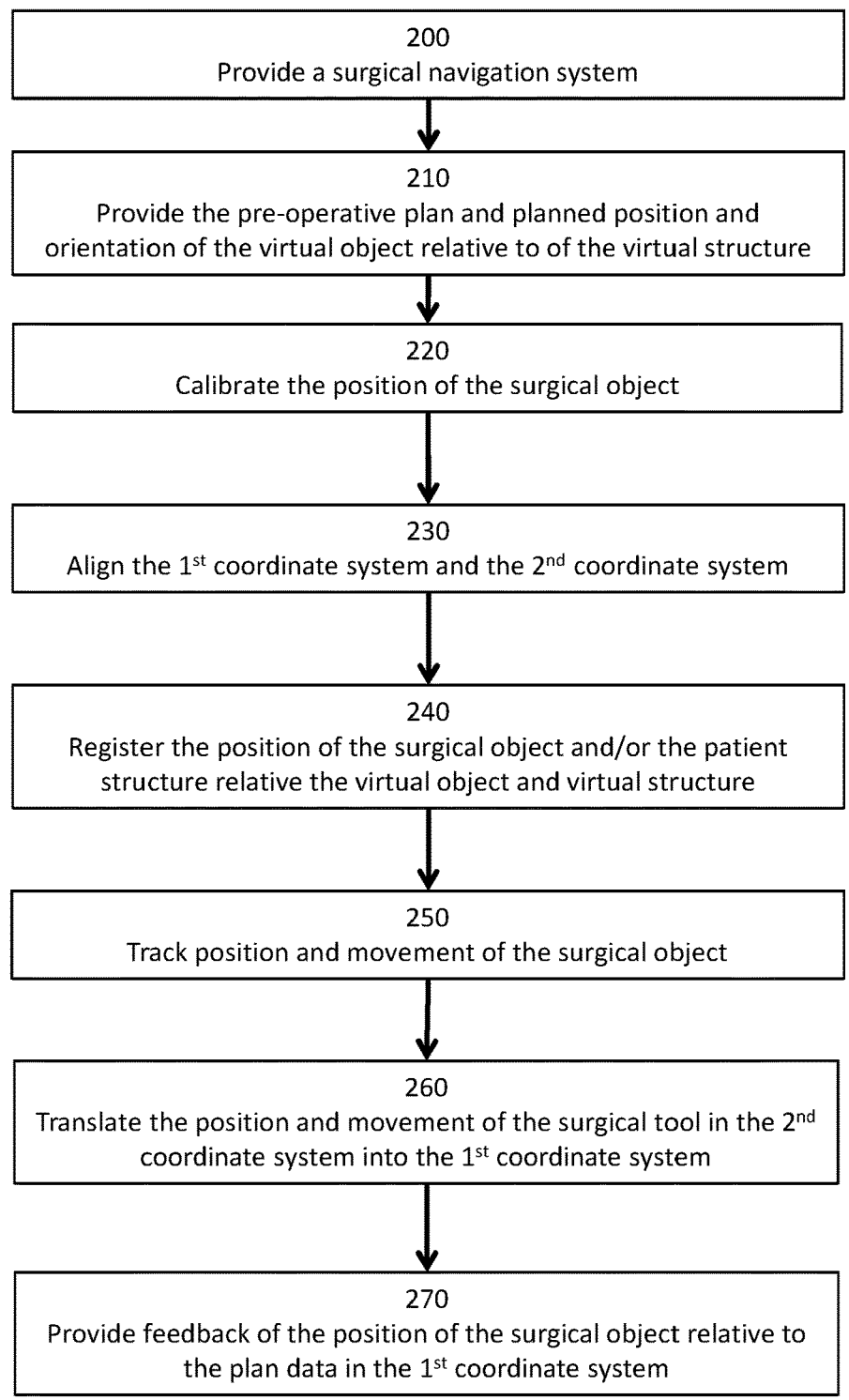
FIG. 6 is a flow chart of an embodiment of a method for tracking the position of a surgical object during surgery and providing feedback relative to the pre-operative plan.

A system and method according to embodiments of the invention comprise a number of components, data and steps. Embodiments of the invention will be described below with regard to various areas in order to structure various components data and steps. It should be noted that in some embodiments, not all areas are included. Furthermore, some areas and/or sub-areas thereof may form independent embodiments, but may not be independently covered by the claims. Embodiments of the invention will be described with regard to the areas: system overview; pre-operative plan; position registration; tracking; and feedback. Embodiments of various methods for pre-operatively planning a surgical procedure is described with regard to various steps, and embodiments of various methods for operating the system according to the invention during surgery is described with regard to various steps, some of which are illustrated in FIGS. 2 and 6.

System Overview

FIG. 1 illustrates an overview of a system for computer assisted orthopedic surgery, according to embodiments of the invention. The system comprises a planning unit 1, at least one position registration unit 2, at least one tracking unit, a communication hub 4, and a feedback device 5. Using the planning unit 1, a pre-operative plan of a surgery may be made before the surgery commences. The pre-operative plan may be based on volumetric scan data obtained from a medical imaging device (not shown), such as a CT (Computer Tomography) or MRI (Magnetic Resonance Imaging) scanner, to obtain patient specific data. From the volumetric scan data, the planning unit 1 can segment various structures, such as bone, to create a 3D model of a patient structure 7, upon which the surgery is to be performed. The 3D model of the patient structure 7 provides a virtual representation of the patient structure, which will be referred to in the following as a virtual structure 8. Additionally or alternatively, the virtual structure 8 may comprise 2D patient data, such as re-slice of the CT data. Creation of a 3D model from volumetric scan data is generally known and will not be discussed in more detail herein. In the embodiments discussed herein, the patient structure 7 may comprise a bony anatomical structure of the patient, such as pelvis, femur, tibia, fibula, or spinal cord. Hence, the system according to the invention is suitable for hip surgery, knee surgery, back surgery etc., wherein planning of the procedure may comprise planning of an extrinsic element is to be introduced in to the patient, such as a hip implant, a knee implant, spinal implant etc.

The planning unit 1 may comprise a computer having software code segments for providing the pre-operative plan. As such, the planning unit may have one or several input devices 9, such as a keyboard and a mouse, and one or several output devices, such as a display 10. Using the patient scan data and the virtual structure 8, the pre-operative plan may be made. The pre-operative plan may comprise planning at least one position and orientation of surgical object 3a, 3b, 3c relative to the patient structure 7 during the surgery. In some embodiments, the surgical object 3a, 3b, 3c comprises an implant, such as a hip implant or a knee implant. Hence, the pre-operative plan may comprise positioning and orienting a virtual representation of the surgical object, referred to as a virtual object 11, to an optimal position and orientation relative to at least one virtual structure 8. An example embodiment would be to position a hip implant relative the femur and orient the head of the hip implant relative to the acetabulum of the pelvis. In relation to a hip replacement, the surgical object, and thus the virtual object, may comprise both the acetabular cup and the femoral component. Thus the pre-operative plan may comprise planning multiple surgical objects, 3a, 3b, 3c, such as the acetabular cup and the femoral component via their virtual representations relative to multiple patient structures, such as the femur and acetabulum. In the embodiment of FIG. 1, planning of a knee surgery is disclosed, wherein the patient structure and the virtual representation thereof may comprise multiple structures, such as the femur tibia, fibula, and/or patella. In this embodiment, the surgical object is a surgical instrument, and planned positions and orientations thereof. Further embodiments of the surgical object and the patient structure will be disclosed below. However, common to these embodiments is the surgical object 3a, 3b, 3c, which is moveable relative to the patient structure 7 during surgery.

The planning unit 1 is adapted to provide the pre-operative plan including planned position and orientation of the virtual object relative to of the virtual structure. Also, the planning unit 1 may be adapted to register the patient structure 7 to the virtual structure 8, and optionally or additionally the surgical object 3a, 3b, 3c to the virtual object 11, as will be disclosed below.

The system provides feedback of at least one surgical object 3a, 3b, 3c relative the pre-operative plan. The pre-operative plan includes the virtual object 11, which is the virtual representation of the surgical object, and a virtual structure 8, which is the virtual representation of the patient structure 7. The virtual object 11 and the virtual structure 8 may be represented as 3D objects, such as 3D surface objects. Hence the planning unit 1 may be a 3D planning unit.

The position registration unit 2 is according to embodiments of the invention adapted to obtain at least one position of the patient structure 7. The position registration unit 2 may operate without any fiduciary markers present in the scan data as well as during surgery. Hence, the patient does not have to go through any operation to place the fiduciary markers before the surgery. Instead, the position registration unit 2 may operate based on the surface of the patient structure, such as the shape thereof, positions of the surface within a coordinate system of the position registration unit 2, etc., as will be discussed further below. The position registration unit 2 may also be adapted to register the position and orientation of the surgical object 3a, 3b, 3c.

A tracking unit 12a, 12b, 12c, which may be attached to the surgical object 3a, 3b, 3c, is adapted to track a current position and orientation of the surgical object 3a, 3b, 3c within a coordinate system and thus relative to the patient structure when they are provided within the same coordinate system or coordinate systems that are registered. The communication hub 4 is adapted to communicate position data from the position registration unit 2 to the planning unit 1, and position and orientation data from the tracking unit 12a, 12b, 12c to the planning unit 1. Hence, the position of the patient structure 7 can be registered by the position registration unit 2 and relayed to the planning unit 1, and registered to the virtual structure 11. Similarly, the position of the surgical object 3a, 3b, 3c can be registered, such as by the registration unit 2 or via docketing station as will be disclosed below, and its position and orientation continuously tracked by the tracking unit 12a, 12b, 12c, and relayed back to the planning unit 1 via the communication hub 4. Furthermore, in some embodiments, the position registration unit 2 is adapted to dynamically update the position and orientation of the patient structure 7, i.e. dynamically reference the patient structure 7 to the virtual structure 8. Hence, the communication hub 4 communicates data to and from the various units in the system. The planning unit 1 may update the position of the virtual object 11 relative the virtual structure 8 based on the tracked position and orientation of the surgical object 3a, 3b, 3c in the coordinate system of the position registration unit 2 or the patient depending on how the system is set up. Hence, the planning unit 1 may dynamically reference the surgical object 3a, 3b, 3c, to a virtual representation of the surgical object and the virtual structure.

In embodiments of the invention, the feedback device 5 is adapted to provide feedback of the current position and orientation of the surgical object 3a, 3b, 3c relative to the planned position and orientation of the virtual object 11 in response to the tracked current position and orientation of the surgical object 3a, 3b, 3c. In some embodiments, the feedback may be provided by a feedback device, such as an indicator, for example a visual indicator, a tactile indicator, or an audio indicator. A visual indicator may e.g. comprise a display, a light emitter, such as one or several LEDs, etc. In the embodiment of FIG. 1, the feedback device 5 is a display of the planning unit 1. Hence, the display may render the virtual structure 8, a representation of the virtual object 11 in its planned position(s) and orientation(s) relative the virtual structure 8, and a representation of the current position and orientation of the surgical object 3a, 3b, 3c relative to the patient structure 7. The representation of the current position and orientation of the surgical object 3a, 3b, 3c relative to the patient structure 7 may e.g. be provided by a virtual 3D model of the surgical object 3a, 3b, 3c. Hence, the visual indicator may be adapted to provide visual feedback of current position and orientation of the virtual object relative to the planned orientation and position of the virtual object based on the tracked current position and orientation of the surgical object. This may e.g. be provided via a display. The visual indicator may be provided at the surgical object, such as integrated therewith, for example within a single chassis of the surgical object. Alternatively or additionally, the visual indicator may be adapted to provide visual indication of the deviation of the current position and orientation of the virtual object relative the planned position and orientation of the virtual object on a screen, and thus between the current position and orientation of the surgical object and its planned position and orientation. This may be provided based on or in response to the tracked current position and orientation of the surgical object. Some embodiments may also comprise a visual indicator adapted to provide visual indication of the deviation of the current position and orientation of the surgical object relative the planned position and orientation of the virtual object, such as via a visual indicator integrated with the surgical object. For example, a multi-colour LED may indicate the deviation from one or several positions and orientations, such as red indicating >50 mm from planned position and orientation, yellow indicating the range 49 mm<>10 mm from planned position and orientation, and green indicating <10 mm from planned position and orientation. Alternatively, the ranges may be indicated using a single colour flashing LED, with different flashing pattern depending on the deviation. In still other embodiments, the feedback device 5 may be acoustic, wherein the pitch, type of signal, etc. of the acoustic signal would indicate the ranges. An acoustic feedback, such as by an acoustic feedback device, may complement or replace the other embodiments for providing feedback. The visual feedback may comprise a cone of acceptance provided via the feedback device 5 in association with the virtual 3D model of the surgical object 3a, 3b, 3c.

FIG. 2 illustrates embodiments of a method for computer assisted orthopedic feedback of at least one surgical object 3a, 3b, 3c relative a pre-operative plan. In step 100, the pre-operative plan including planned position and orientation of the virtual object relative to the virtual structure is provided, such as using the planning unit 1. In step 110, the position of the patient structure is obtained, which may be based on a surface of the patient structure, such as using the position registration unit 2. In step 120, the position of the surgical object 3a, 3b, 3c is obtained, such as using the position registration unit 2 or a docketing station to track the position and orientation of the surgical object 3a, 3b, 3c. In step 130, the patient structure 7 is registered to the virtual structure 8. The surgical object 3a, 3b, 3c may be registered to the virtual object 11. Alternatively or additionally, the surgical object may be calibrated for tracking its position relative the virtual structure and/or planned positions of the surgical structure i.e. planned positions of the virtual structure relative actual positions of the virtual structure. In some embodiments, the surgical object 3a, 3b, 3c is registered to the virtual object 11 and/or calibrated prior to the surgical procedure commences, and thus prior to registration of the patient structure 7. In step 140, the current position and orientation of the surgical object 3a, 3b, 3c is tracked. When the surgical object 3a, 3b, 3c and the patient structure 7 are located in the same coordinate system, or in coordinate systems that are referenced, position and orientation of the surgical object will thus tracked the relative to the patient structure 7. In step 150, feedback of a current position and orientation of the surgical object relative to the planned position and orientation of the virtual object is provided based on the tracked current position and orientation of the surgical object. The feedback may be provided as discussed above with regard to the feedback device 5.

In some embodiments, step 140 comprises tracking the current position and orientation of the patient structure, and compensating the current position and orientation of the virtual object based on the tracked current position and orientation of the patient structure. This may e.g. be provided if the coordinate system is fixed to the patient structure, and the position and orientation of the surgical object is tracked within that coordinate system. Dynamic referencing may also be provided, wherein the position of the patient structure 7 is dynamically tracked.

Pre-Operative Plan

Before the surgery commences, planning data from the pre-operative plan is provided. The planning data includes patient structure plan data, and surgical object plan data, such as the virtual representations thereof. This may be provided in a first coordinate system, i.e. the coordinate system of the planning unit 1. The virtual object 11 and the virtual structure 8 may have a fixed positional relationship within the first coordinate system when the planning is completed.

The pre-operative plan may comprise a number of steps in order to reach the position and orientation data for the virtual object 11. This may comprise accessing volumetric scan data that comprises patient structure scan data; converting the patient structure scan data into the virtual structure 8, which may comprise a three dimensional representation of the patient structure 7; generating, based on user interaction, a plan of at least one position and orientation of the virtual object 11 relative to the virtual structure 8; registering the planned position and orientation of the virtual object 11; and including at least one of the scan data and the three dimensional model of the virtual structure 8 together with the planned position and orientation of the virtual object 11 in the pre-operative plan. If the scan data is included together with the planned position and orientation of the virtual object 11 during planning, the virtual structure may be recreated in the planning unit 1 before surgery. Hence, the planning unit 1 may be a separate unit from a planning station upon which the pre-operative plan was made. Still, the surgeon may have access to the same data as during the planning, such as the 3D model of the patient structure, scan data, such as CT or MRI data that can be re-sliced during surgery to provide further information to the surgeon. Alternatively, the virtual structure is included together with the planned position and orientation of the virtual object. Hence, in some embodiments, only the virtual object 11 and virtual structure 8 are available during the surgery. This may also be provided in different windows of the display, in which the pre-operative plan and feedback to the surgeon during surgery is provided.

In some embodiments, the pre-operative plan comprises planning a cut of a patient structure, such as to separate a femur head from the femur for a hip implant surgery. In this context, it may be desired that the femur has a certain position and orientation relative to the pelvis or a portion thereof, such as the acetabulum. Hence, in this context, the surgical object may comprise at least one bony anatomy of the patient. Furthermore, the surgical plan may comprise planning of a surgical template for guiding a surgical procedure, such as a cut of the femur head. In this context, the surgical object may comprise a surgical template having at least one surface with a shape that conforms to the shape of the bony anatomy of the patient. For hip surgery, multiple patient structures and/or surgical objects may be provided, such as a bony anatomy and a surgical template. Additionally or alternatively, the surgical object may comprise a surgical instrument and its position and orientation relative to the patient structure at one or several instances during the procedure. This may e.g. be provided to give visual indications of cuts, drilling operations, etc. such that the surgeon is visually guided to an optimal and pre-planned path for the instrument. However, the actual movement of the instrument is still completely in the hands of the surgeon, who is fully in control of the surgery. The instrument may be a hand-held surgical instrument. Furthermore, the surgical object may comprise an implant for implantation into the patient structure, such as a hip implant including a femur component, and optionally also an acetabular cup.

Generating scan data of a patient is generally known. The scan data may comprise DICOM data obtained from, for example a medical imaging scanner, such as a CT scanner, MRI scanner, or an X-ray scanner. The scan data may be supplied in one or multiple files. The scan data comprises a 3D volume of data out of which 2D slices of information can be generated during planning. Hence, the surgeon can virtually cut through the anatomy of the surgical object in order to plan position and orientation of the surgical object 3a, 3b, 3c, such as one or multiple positions and orientations of a surgical instrument, positions and orientations of implant components, and positions and orientations of surgical templates.

Figure 3:
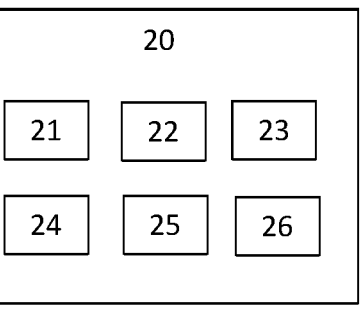
FIG. 3 is a block diagram of an embodiment of a computer system for preparing a pre-operative plan.

FIG. 3 illustrates a computer system 20, in which the scan data may be imported. The computer system may also be used during surgery as the planning unit 1, wherein the position data of the surgical object may also be accessed. Alternatively, a separate planning unit 1 is provided during planning, wherein the computer system 20 used during planning does not need capability to access the current position data of the surgical object. The computer system 20 comprises a CPU or data processing unit 21, one or several memories 22, a communication unit 23, a reading unit 24 for reading the scan data, an input device 25, such as a mouse and/or a keyboard, and a feedback device or an output unit 26, such as a display. Furthermore, the computer system 20 may comprise computer software for performing a pre-operative plan. The computer software may comprise a CAD system, wherein the scan data can be rendered, such as a 3D model of the surgical object, and/or 2D slices of original scan data, such as MRI or CT data. The 3D model of the surgical object and the 2D scan data may also be rendered at the same time and be partially overlaid in order to increase the information. The CAD system may comprise a general purpose CAD system, such as 3 ds Max from Autodesk®.

Once the scan data has been imported, a 3D model of the surgical object 11 can be provided. The 3D model may e.g. be a 3D surface model or a point cloud created using a 3D graphics technology.

Figure 4:
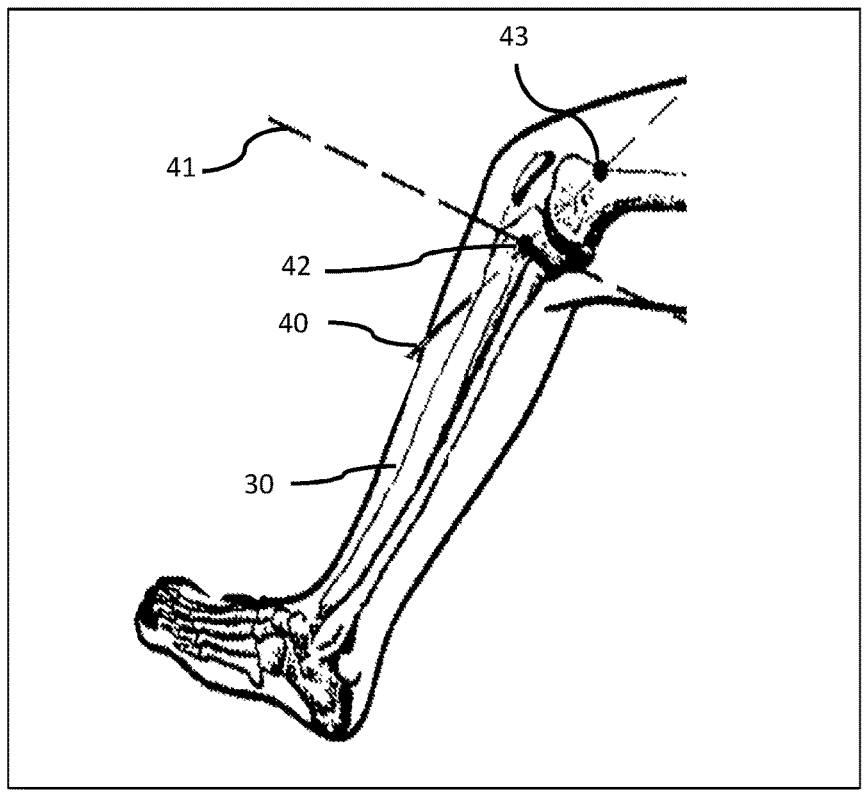
FIG. 4 is a front-view of a display in which a pre-operative plan is illustrated.

FIG. 4 illustrates an embodiment of planning a surgical procedure and providing a pre-operative plan. When accessing the scan data, the scan data may comprise patient structure scan data. The patient structure scan data may be converted into the virtual structure 30, which is the virtual representation of the patient structure. At least one position and orientation of the virtual object relative to the virtual structure 30 is planned for the surgical procedure. In some embodiments, multiple positions and/or orientations of the virtual object relative to the virtual structure are planned. Furthermore, positions and/or orientations for multiple virtual objects may be planned, for example if different surgical objects are used during the procedure.

In some embodiments, planned positions and orientations of the virtual object may form the positions and orientations of one or several paths of the virtual object. In the embodiment of FIG. 4, a first path 40 and a second path 41 are illustrated. The path 40, 41 may e.g. be formed by an entry position 42 and an end position 43, which may be indications for entry and end, respectively, positions of an end-effector of the surgical object, such as the entry and end positions of a drill, such as the tip thereof. The path may then comprise a straight line between the entry position 42 and the end position 43, which inherently also may provide the orientation of the path 40, 41. The straight line does not necessarily need to be registered, but can be generated when needed as the entry position 42 and the end position 43 are enough information to generate a straight path. If the path is curved, one or several additional positions between the entry position 42 and the end position 43 may be marked and registered. A line may then be generated between any two positions, preferably two neighboring positions. In other embodiments, a single position of the surgical instrument is planned, such as an entry position 42 or an end position 43. In other embodiments, the virtual object is a 3D object for indicating a region for harvesting bone, such as for insertion of a femur component or acetabular cup, for example a virtual representation of the femur component and/or acetabular cup.

In the embodiment of FIG. 4, a knee surgery is illustrated. Surgical objects are provided in the form of information for a path for a surgical instrument, such as a surgical drill. Optionally, the pre-operative plan may also comprise virtually positioning and orienting an implant for the knee surgery. The first path 40 has been planned. The first path 40 has been planned by indicating with an object the entry position 42 and the end position 43. The first path 40 is in this embodiment a straight line between the entry position 42 and the end position 43. In this embodiment, the second path 41 has also been planned. The first path 40 has been generated by generating a line using the input device 25. Then, the line has been positioned, again using the input device 25, such that the second path 41 passes through the entry position 42. Hence, two or more paths may share one or several planned positions and/or orientations, such as an entry position 42 and/or an end position 43 of the surgical instrument.

Figure 5:
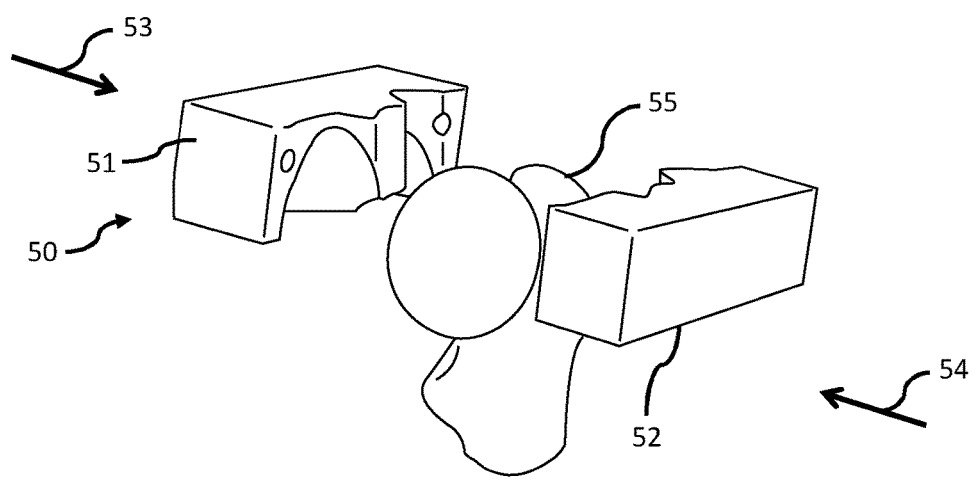
FIG. 5 is a perspective view of a surgical template.

In other embodiments, different positions of a surgical template 50 relative to other structures, such as relative to a bony anatomical structure, are planned. FIG. 5 illustrates an embodiment of the surgical template 50. The surgical template 50 is a multi part 51, 52 surgical template, that has been planned to facilitate assembly from a first assembly direction 53 and a second assembly direction 54 of the surgical template 50. During surgery, such as when the head of the femur 55 is to be cut for a hip surgery, the position of the surgical template 50 may be planned to have a particular position and/or orientation relative at least a portion of the pelvis (not shown), and/or a portion of the femur. Hence, the position and orientation of the surgical template 50 relative the bony anatomy of the patient at the time when a portion of the femur is cut may be planned. In another example, during knee surgery, the surgical template (not illustrated) may have a first position and orientation relative to the tibia and/or fibia during a first stage of the surgery, and a second position and orientation relative to the tibia and/or fibia during a second stage of the surgery (which may also include positioning and orienting multiple surgical template for this purpose). In such a situation, the planning software may comprise simulation capabilities, wherein movement of different structures of the 3D model of the patient can be simulated. Hence, for a first stage of the surgery, a first positions of the surgical template 50, and/or a first position of a surgical instrument, relative the virtual structure or structures can be planned, wherein the different virtual objects have a first positional relationship relative to the virtual structure. Movement of a virtual structure is simulated such that the different parts of the virtual structure have a second positional and orientation relationship. Then, a second position and orientation of the surgical template, and/or a second position and orientation of the surgical instrument, can be planned, such as a second path and/or a second position and orientation of the surgical template 50.

In other embodiments, a dental procedure may be planned. For example, the position of a dental implant in the jawbone may be planned. The position and orientation of the dental implant may, e.g., be planned by positioning a virtual object representing the dental implant. In its planned position, the head of the dental implant marks the entry position for a drill, and the tip of the dental implant marks the end position for the drill. The path is a straight path between the entry position and end position. Furthermore, the distance between the entry position and the end position, and/or the type and size of dental implant, may indicate the length and/or diameter of a corresponding surgical object, which in this embodiment may comprise a drill. The dental implant may comprise a screw type dental implant. Similar types of procedures may also be planned for other straight implants similar to dental implants, such as an implant for spinal fusion.

Once the planning of the surgical procedure is complete, the pre-operative plan is provided 100. The pre-operative plan may comprise the scan data with the planned positions and orientations for the surgical object in a first coordinate system in a fixed relationship. Alternatively or additionally, the pre-operative plan may comprises the 3D model of the patient structure 30 together with the planned positions for the surgical object in the first coordinate system in a fixed relationship. Any of these data sets is referred to as the pre-operative plan.

The pre-operative plan may be provided at the time of surgery. During surgery, the computer system 20 may be provided, wherein the virtual structure representing the patient structure 30 can be recreated from the scan data. Alternatively, the virtual structure 30 representing the patient structure and the planned positions and orientations of the virtual object are provided in the same coordinate system in the planning data, wherein optionally also the scan data may be provided.

The computer system 20 may comprise the first coordinate system, in which the virtual structure and the planned positions and orientations of the virtual object in relation thereto are provided, such as the planned paths 40, 41. For example, the first coordinate system may be the coordinate system of a CAD software where the scan data, virtual structure, and the virtual object are present or provided.

Included in the pre-operative plan may also be supplied surgical object information, such as concerning type, and/or size, such as length and/or diameter, of the surgical object. For example, the surgical object may comprise a drill, such as a bone drill for orthopedic or dental drilling. Hence the surgical object type is drill. If various sizes for the drill may be planned, the size of the drill may be included in the planning data. In other embodiments, the surgical object is a mill, a saw, etc. Hence, each virtual object, such as a planned path and/or position thereof, may be associated with surgical object information.

According to embodiments of the invention, surgical objects may e.g. comprise a surgical template, a drill, a saw, a cutter, and/or a dental hand piece.

Position Registration

According to embodiments of the invention, position registration unit 2 is a surface based position registration unit. Surface-based registration is highly accurate and reliable, and does not require any surgical procedure prior to the surgery of the patient structure. Using this technique for registration, a cloud of surface points on the patient structure may be collected using a tracked probe. The positions from the surface of the bone having a unique shape are then used to match the pre-operative plan with the position of the patient in the operating room. Hence, the patient structure may be registered to the virtual structure using this technology. Furthermore, an initial position of the surgical object may be obtained using this technology, and then registered to the virtual object. Any deviation between the actual position of the surgical object and the planned position of the virtual object may be indicated via the feedback device 5.

The planning unit 1 may be adapted to import the point cloud, such as in any of the file formats iges, step, and stl. Furthermore, the surface data of the patient structure may also be provided as volumetric data, such as voxel data. Furthermore, the planning unit may be adapted to make coordinate transformations, Union cross sections, and Boolean operations. Furthermore, the planning unit may be adapted to provide matching operations, such as surface or volume matching.

The position registration unit 2 may be adapted to obtain the position of the patient structure using a first navigation system such as a 3D-6D navigation system having a first accuracy. If the coordinate system during the operation is affixed to the patient structure, it is only necessary to use a 3D navigation system to register the position of the patient structure to capture the spatial location in three degrees of freedom. If the coordinate system is not affixed to the patient structure, also the orientation of the patient structure in the coordinate system may be obtained, whereby a 6D navigation system may be used for the additional degrees of freedom roll, yaw, pith. Furthermore, the position registration unit 2 may be adapted to obtain the position and orientation of the surgical object using a second navigation system, such as a 6D navigation system. The navigation system to obtain the position of the patient structure may be the same or different than the navigation system to obtain the position and orientation of the surgical object. The second navigation system may have a second accuracy, which is equivalent or higher than the accuracy of the first navigation system. Hence, it will be possible to track the position and the orientation of the surgical object relative to the patient structure. The first accuracy is preferably better than a mean deviation of 0.2 mm, even more preferably better than 0.1 mm.

The navigation systems may e.g. be an optical navigation system. In one embodiment, the navigation system is an image guided navigation system that comprises a tracked probe with embedded light sources, such as LEDs, providing a navigation unit as will be further discussed below. Positions on the surface of the patient structure may be registered and enough surface points obtained for the registration. A system for obtaining the shape or point cloud is e.g. disclosed in WO91/16598, which is incorporated herein by reference for all purposes. Point by point measurements may also be made using a touch probe to collect spatial positions of a surface for a point cloud, such as is disclosed in U.S. Pat. No. 5,440,392, which is incorporated herein by reference for all purposes. Another embodiment of an optical navigation system is disclosed in U.S. Pat. No. 6,166,809, which is incorporated herein by reference for all purposes, with which both position and orientation may be obtained.

According to embodiments of the invention, optical navigation systems may be used to obtain the position of the patient structure. When positions from the surface of the patient structure has been obtained, the point cloud may be used to register the patient structure to the virtual structure. The registered information about the surface is compared with the virtual structure, such as in the form of a 3D surface model. A registration matrix between the two surfaces may be computed using iterative closest point (ICP) algorithm . After the transformation, the positional relationship between the patient structure and virtual structure is obtained. Registration of the surgical object relative the virtual object may be made in the same way as the patient structure relative the virtual structure. The registration matrix may comprise a transformation matrix including translation and rotation identities, such as x, y, z translation identities and roll, pitch, yaw identities.

In some embodiments, the position registration unit comprises a sensor and a receiver. In some embodiments the position registration unit is an optical tracking system, wherein the sensor may comprise and passive or active sensor, such as a fiducial marker and/or a LED, and the receiver is an optical receiver, such as one or many cameras. In other embodiments, the position registration unit comprises a transmitter and position determination unit, wherein the position in space relative a known location is registered and transmitted to a receiver in the system. The sensors, transmitters, position determination units are collectively referred to as navigation unit herein. Tracking unit 12a, 12b, 12c may each comprise a navigation unit, such as one or several sensors, transmitters, and/or position determination units, based on the technologies as described herein, such as optical components, MEMS, gyros, accelerometers, etc.

In some embodiments, the surgical object comprises a detachable navigation unit, such as tracking unit 12a, 12b, 12c. The navigation unit may be attached and detached to the to the surgical object in a single repetitive position. The detachable navigation unit may be connected to the surgical object via a connection interface or reference surface, which may have one or several projections and recesses such the navigation unit fits to a connection interface or reference surface of the surgical object having a complementary shape. Hence, the detachable navigation unit fits to the surgical object only in a singe pre-defined position. Furthermore, the navigation unit may comprise information about the surgical object to which it is attached, such as a position of an end effector of the surgical object, e.g. the tip of a drill or milling tool, relative the connection interface of the surgical object. Hence, by determining the position and orientation of the connection interface of the surgical object or the position and orientation of the navigation unit, the position and orientation of the surgical object may be obtained. This information may be transferred to the communication hub 4, such as via a wireless communication device, such as using WiFi or Bluetooth® technology. In some embodiments, the navigation unit to be attached to the surgical object may be based on the optical navigation systems referred to above.

The registration of the acquired positions from the patient structure and/or the surgical object may be made using, e.g. a best-fit registration, surface fit registration etc. Algorithms for this purpose are generally known and will not be further disclosed herein. However, it should be noticed that it is important that the surface positions are obtained from an area represented in the virtual structure. For example, if the patient scan is made using CT, the surface should be a bone surface and not a cartilage surface, which is normally not the surface which forms the basis for the 3D model, but rather the bone surface. However, if the patient scan is made using MRI, the surface from which positions are captured may comprise a cartilage surface. However, if the patient scan comprise both types of scan data, this may not be an issue.

Figure 7:
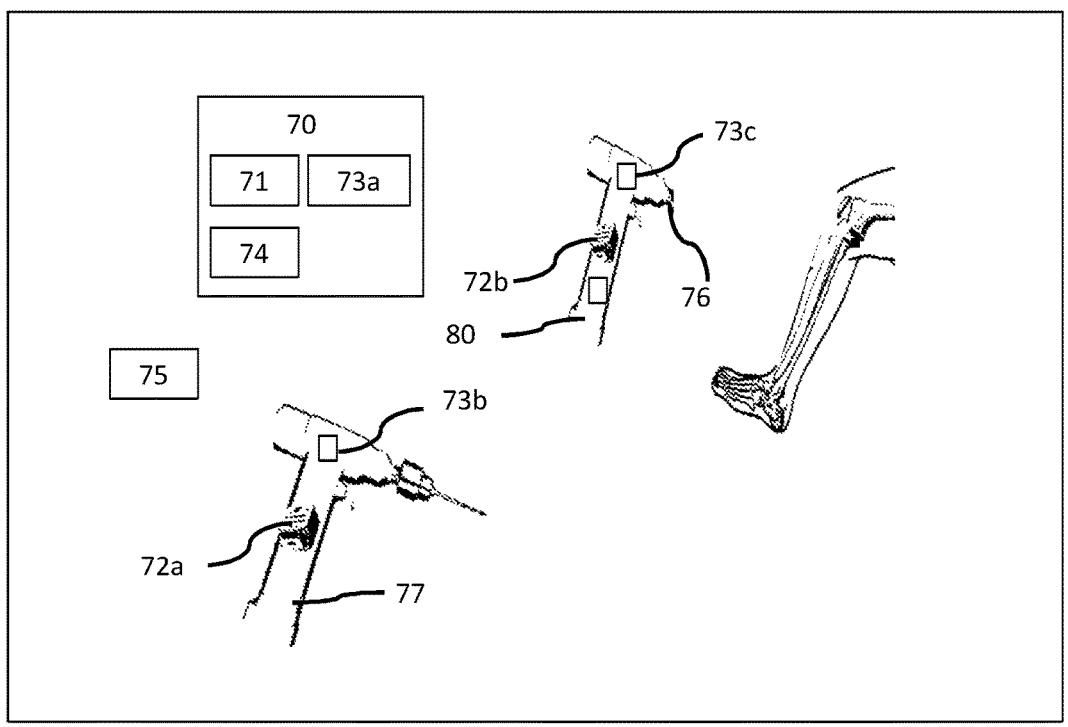
FIG. 7 is a block diagram and a schematic view illustrating an embodiment of a navigation system used during a surgical situation.

FIG. 6 illustrates a method for tracking the position of the surgical object illustrated as a surgical instrument using a surgical navigation system 70 illustrated in FIG. 7. In step 200, the surgical navigation system 70 is provided. In step 210, the pre-operative plan and planned position and orientation of the virtual object relative to of the virtual structure are provided. The surgical navigation system 70 is provided within the surgical theatre or operating room. The surgical navigation system 70 comprises a calibration unit 71 and is associated with or comprises a second coordinate system. Hence, the calibration unit 71 has a fixed position within the second coordinate system when it is used for calibrating various instruments and devices as will be described below. The calibration unit 71 may be provided as a docking station, within which the origin of the second coordinate system may be provided. The calibration unit 71 is provided to calibrate the position of the surgical object 77, or the navigation unit thereof, a detachable navigation unit as discussed above, and/or other tools, as will be described below, within the second coordinate system. In more detail, each surgical object 77 may comprise a navigation unit 72a, 72b. Before the surgery commences, the position of the navigation unit 72a, 72b may be calibrated, such as illustrated in step 220, i.e. its position and orientation within the operating room may be registered. The position and orientation of the navigation unit 72a, 72b relative to the surgical object 77, such as an end-effector, may be known or calculated. For example, the position and orientation of the navigation unit 72a, 72b may have a fixed position and orientation relative an end effector of the surgical object 77, or may be calculated as will be further described below. After calibration of the position and orientation of the navigation unit 72a, 72b is made, the position and orientation of the navigation unit 72a, 72b, and hence the position of the surgical object 77, may be tracked in space as will be discussed in more detail below.

Furthermore, the surgical navigation system 70 comprises the communication hub. The communication hub may comprise first a communication unit 73a connected to a data processing unit 74. The data processing unit 74 may be connected to the planning unit 75 that may be designed similar to computer system 10 described in relation to FIG. 3. The surgical object 77 may comprise a second communication unit 73b, for communicating the tracked position and orientation of the surgical object to the data processing unit 74. The communication system may e.g. be a short-range wireless communication system, such as a Bluetooth® or a WiFi communication system.

The surgical navigation system 70 may be an inertial navigation system (INS), which continuously can calculate the position, orientation, and velocity (direction and speed of movement) in 3D space of the surgical object and/or a position registration unit 80 (FIG. 7), such as the tracked probe. Hence, once the position and orientation of the surgical object 77 and/or the position registration unit 80 has been calculated, the direction and speed of movement can be tracked. For this purpose the navigation unit 72a, 72b may comprise angular accelerometers to measure how the surgical instrument and/or the position registration device is oriented in space. There may be one angular accelerometer for each axis, i.e. roll, yaw and pitch. Furthermore, the navigation unit 72a, 72b may comprise a linear accelerometer for each axis, up & down, left & right, and forward & back to track the spatial position. Together the six degrees of freedom can be tracked. The data processing unit 74 can be arranged to calculate the current position and orientation of the surgical object 77 and/or the position registration unit 80. Alternatively, a data processing unit is integrated together with the navigation unit 72a, 72b and integrated with the surgical object 77 and/ or the position registration unit 80.

In some embodiments, the navigation unit 72a, 72b comprises an inertial measurement unit (IMI) that uses a combination of accelerometers and gyroscopes to report the surgical object's and/or the position registration unit's velocity, orientation, and gravital forces. In some embodiments the IMI is a wireless IMI (WIMU). The IMI sensor allows the data processing unit 74 to compute the position and orientation of the surgical object and/or the position registration unit via e.g. dead reckoning calculations.

In some embodiments, the navigation unit 72a, 72b is built on Micro Electro-Mechanical System (MEMS) technology. Such a navigation unit 72a, 72b may comprise a multi-axis gyro module with up to three axes of highly accurate MEMS gyros and/or accelerometers. Such modules are for example available from Sensonor, Norway. For example, the STIM210 module provides sufficient accuracy for use in embodiments of the surgical navigation system according to the invention. Alternatively, MEMS inertial motion sensors for integration with the system according to embodiments of the invention are available from IMEGO AB, Sweden.

Designing an INS is for example described in DESIGN OF AN INERTIAL NAVIGATION UNIT USING MEMS SENSORS, by Maksim Eskin, Project Advisor: Bruce Land Degree, Date: January 2006, which is incorporated herein by reference for all purposes.

Registration

As is illustrated in FIG. 7 the navigation system 70 may comprise the position registration unit 80. The position registration unit 80 is configured to register positions on the surface of the patient structure. In some embodiments, the position registration unit 80 is completely separate form the surgical object, such as illustrated in FIG. 7. In other embodiments, the position registration unit 80 is provided together with the surgical object 77, such as within the same chassis.

The position registration unit 80 comprises a navigation unit 72b, and a communication unit 73c, configured as the navigation unit 72a and the communication unit 73b of the surgical object 77 disclosed above. Hence, the position of the position registration unit 80 within the second coordinate system may be tracked and communicated to the data processing unit 74. If the position registration unit 80 and the surgical instrument 77 are provided as a single unit, they may share the same navigation unit and communication unit.

The position registration unit 80 comprises a position registration probe 76. Hence, the position registration unit may form a tracked probe. The position registration probe 76 is configured to determine and register positions of patient structure within the second coordinate system, such as to capture a point cloud, illustrated in step 240. The positions of patient structure can be determined by their coordinates within the coordinate system. The positions of the of the patient structure surface can be registered using e.g. projection technology, wherein a laser patter is projected by the position registration probe 76 onto the physical landmark, and whereby the shape of the pattern when projected can be recognized and the location of the surface position relative the position registration unit 76 may be determined. In other embodiments, the position registration unit 76, and or the surgical instrument, comprises computer vision technology and uses image analysis for identifying the positions of the surface of the patient structure. The image data may e.g. be acquired using a camera taking multiple images, a video camera, or multi dimensional data from a medical scanner. In still other embodiments, the position registration probe 76 is a holographic position determination unit. Such a unit may e.g. be provided using conoscopic holography, which may use a holographic technique based on light propagation effects in uniaxial crystals. Such technology has previously been used in 3D scanners for scanning 3D objects in order to record the shape thereof, but has previously not been used in a navigation system for registering the position of a patient structure. The position registration probe 76 has a fixed known position relative the navigation unit 72b. Hence, tracking the position of the navigation unit 72b also tracks the position of the position registration probe 76. By registering the position of the patient structure surface relative the position registration unit 76, the former's coordinates may be determined. In still other embodiments, the position registration probe 76 comprises optical registration technology, such as discussed above.

Providing the position registration unit 80 integral with the surgical object 77 has the benefit that the position of the patient structure can be registered in real time during the course of the surgical procedure. Hence, if the patient structure unexpectedly moves during the surgery, this is detected and fed back to the data processing unit 74. Hence, the combined surgical object and position registration unit comprises a position registration unit, a navigation unit, and a communication unit for wireless communication. Thereby, the tool is very flexible, and its position in space can be tracked without being limited by any mechanical arrangement, as is the case in robotic surgical systems.

According to embodiments of the method of the invention, the position of the patient structure is registered within the second coordinate system by means of the surface thereof. The patient structure surface has corresponding position relative to the surgical object as the surface of the virtual structure relative to the virtual object in the pre-operative plan.

Registering the position of the patient structure by means of the surface thereof within the second coordinate system may comprise calibrating the position registration unit 80 within the surgical navigation system by docketing the navigation unit 72b of the position registration unit to a known position of the calibration unit 71 in the surgical navigation system 70. This may e.g. be done in the same way as calibrating the surgical tool, as has been described above. Then, movement of the position registration unit in the second coordinate system is tracked using the navigation unit 72b of the position registration unit 80. Positional information of the surface of the patient structure in the surgical navigation system, i.e. in the second coordinate system is registered using the position registration unit 80, such as the position registration probe 76 thereof. The registered positional information may be communicated to the data processing unit 74. The registration of the patient structure to the virtual structure may be made as discussed above, wherein the coordinate system of the pre-operative plan and the coordinate system of the patient or navigation system are registered.

In still alternative embodiments, the surface information of the patient structure is provided using a volumetric scanner, from which the surface informational may be segmented. Then, matching to the virtual structure may be performed as discussed above.

Tracking

Figure 8:
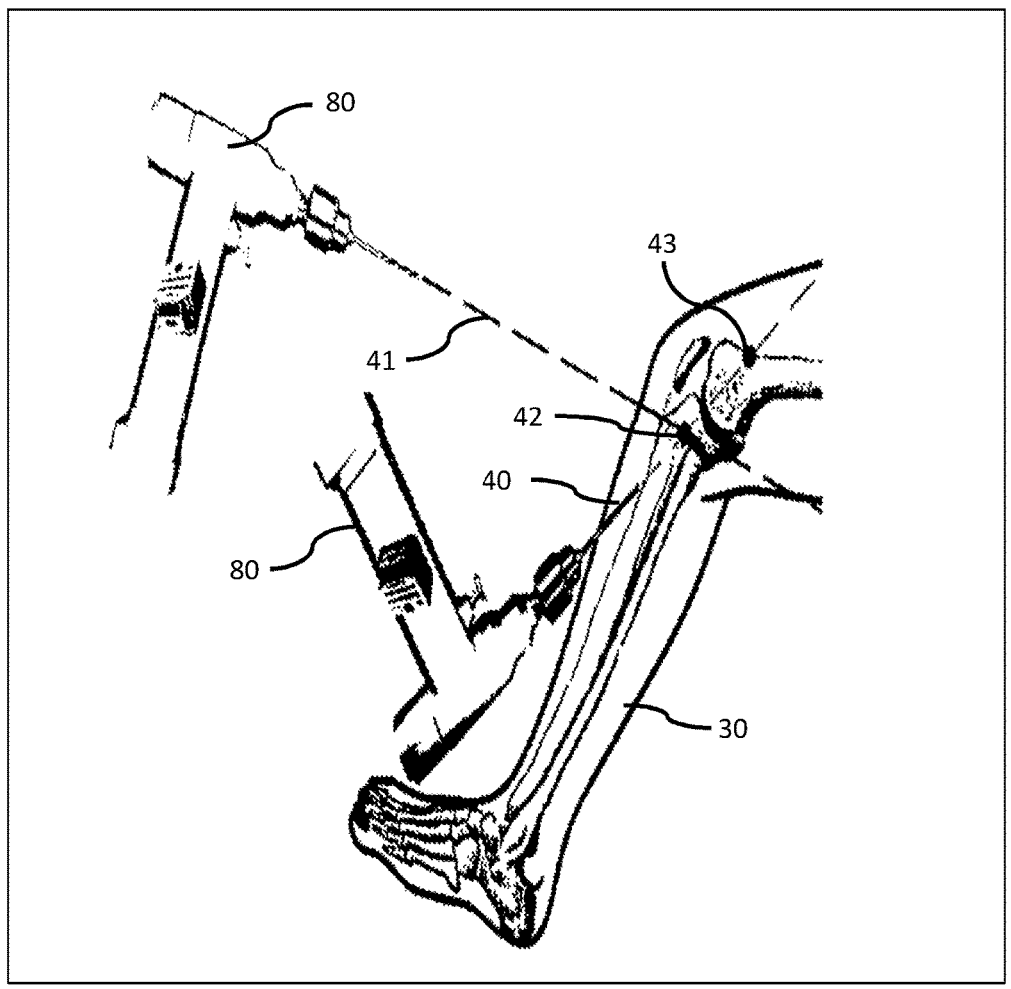
FIG. 8 is a schematic view of a display illustrating an embodiment of displaying the tracked position and orientation of the surgical object relative to the pre-operative plan.

FIGS. 7 and 8 illustrate the tracking, also referred to as dynamic referencing, of the position and orientation of the surgical object 77, also illustrated by step 250 of FIG. 6. In order to provide the information concerning the tracked position and orientation of the surgical object into the pre-operative plan, the first coordinate system and the second coordinate system are aligned in step 230. Hence, a position in space in the second coordinate system is translated into an indication of the position in the first coordinate system, such as illustrated by step 260 of FIG. 6. The first coordinate system and the second coordinate system may be aligned by generating a relationship between the position information of the surface of the patient structure within the first coordinate system and the position of the corresponding virtual structure within the second coordinate system. In the first coordinate system, the position and optionally orientation of the virtual structure is known or can be calculated from the planning data. The position and optionally orientation of the corresponding patient structure are known from the registration process 220 described above. Hence, using this knowledge, it is possible to set up a coordinate transformation matrix, whereby the first coordinate system and the second coordinate system may be aligned. Hence, the first coordinate system and the second coordinate system may be aligned making use of the patient structure and the corresponding virtual structure. Using the coordinate transformation matrix, a position and orientation of a patient structure or surgical object in the second coordinate system can be translated into an indication of the position and orientation in the first coordinate system. Setting up a coordinate transformation matrix in generally known, and is e.g. described in Global Positioning Systems, Inertial Navigation, and Integration, Mohinder S. Grewal, Lawrence R. Weill, Angus P. Andrews Copyright 5 2001 John Wiley & Sons, Inc. PrintISBNO-471-35032-X ElectronicISBNO-471-20071-9, Appendix C—Coordinate Transformations, which is incorporated herein by reference for all purposes. Hence, translating a position and orientation in the second coordinate system into an indication of that position in the first coordinate system may comprises translating using the relationship between the position of the surface of the virtual structure within the first coordinate system and the position of the corresponding patient structure within the second coordinate system, which may be done using the coordinate transformation matrix. This is different from robotic surgical systems, wherein the patient is registered into the coordinate system of the robot, which in turn has a fixed relationship to the coordinate system of the planning, since the robotic arms are fixed to a frame having an origin that is already aligned with the origin of the planning system. According to embodiments, the surgical object has no mechanical connection to the origin of the second coordinate system and can be freely moved, the coordinate systems first has to be aligned before feedback of the movement can be indicated in relation to the planning data, such as illustrated by step 260 of FIG. 6. However, this provides superior flexibility of movement of the surgical tool during surgery since it can be moved in all degrees of freedom without any restrictions by mechanical linkage or wires. Furthermore, additional guidance is provided to the surgeon by the feedback of the position and orientation of the surgical object relative to the planned position and orientation of the corresponding virtual object in the pre-operative plan. Also, tracking of movement of surgical templates etc. is not possible in the robotic systems, but is according to embodiments of the invention.

For such tracking, a connection interface may be included into the planning, which may have the same shape as the connection interface described above with regard to the detachable navigation unit. Hence, the position of the connection interface may be planned relative to the virtual object and/or the virtual structure, such that it does not interfere with the surgical procedure. Hence, when the connection interface is located in its planned position and orientation during surgery, the planned position and orientation of the surgical template relative the virtual object and thus the patient structure has been obtained.

When the first and the second coordinate systems have been aligned, the position and orientation of at least one surgical object within the second coordinate system can be tracked in step 220 using the surgical navigation system. The tracked position and orientation of the surgical object within the second coordinate system can be translated into positional and orientation information in the first coordinate system. The translation may e.g. be made by the data processing unit 74; alternatively, the translation may be made by a processing unit in the computer system 10 wherein the planning was made or a similar system such as planning unit 75. Basically, since the data concerning the movement can be freely communicated, the actual translation of the movement in the second coordinate system can be made depending on computational efficiency and/or depending on the type of positional information to be indicated in the first coordinate system. The position and orientation of the surgical object within the second coordinate system can be calibrated, as has been described above, by docketing the navigation unit 72a, 72b of the surgical object and/or the position registration unit 80 to the calibration unit, which has a fixed known position in the second coordinate system. Then, the position of the surgical object and/or the position registration unit 80 is tracked by means of the navigation unit 72a, 72b. The position and orientation may be tracked e.g. by comparing consecutive measurements of the coordinates of the surgical object 77. Any difference between the consecutive measurements is an indication of a movement. The tracked movement, such as consecutive coordinates of the surgical object, may be communicated from the surgical object to the data processing unit 74. Tracking movement of the surgical object may 77 comprise tracking movement using at least one gyro and at least one accelerometer or an optical tracking system to generate positional data as has been described above. Furthermore, the communication of the positional and orientation data from the surgical object 77 to the data processing unit 74 may be made wirelessly via the communication units 73a and 73b. Furthermore, the surgical object may comprise a surgical tool or a surgical template, the position or positions and/or orientation of which has been planned. Hence, tracking the position and/or orientation of the surgical instrument may comprise tracking the position and/or orientation of at least one of a surgical tool and a surgical template within the second coordinate system, and subsequently displaying the indication of a position and/or movement of at least one of the surgical tool and the surgical template within the first coordinate system. In other embodiments, positions of one or several surgical tools and/or one or several surgical templates are tracked in the second coordinate system, and the position and/or movement is translated into an indication of the position and/or movement in the first coordinate system.

The first coordinate system and the second coordinate system may comprise a polar and/or a Cartesian coordinate system.

Position and orientation information may be transmitted between the units of the system at a frequency that is higher than 2 Hz, preferable higher than 10 Hz. The communication hub may have a computational power to be able to calculate and update the position and orientation at a frequency of 2 Hz, preferably 10 Hz, from all units to which it is connected. Hence, the feedback to the surgeon will be updated sufficiently such that corrections regarding the position and the orientation of the surgical object may be made based on all units that are operative in the system during the procedure. Hence, the communication hub 4 is adapted to communicate the information between the various units to which is connected at this frequency. The communication hub 4 may, hence, substantially communicate the position and orientation of a surgical object and a patient structure in the coordinate system in which it is located to all other units to which it is connected. Hence, positional and orientation information may be communicated between surgical objects and position registration units present in the system. On a display, such as display 5, it is possible to follow the position of all units in the system in relation to the patient structure or structures as well as the relative positions between the various units.

Feedback

Figure 9:
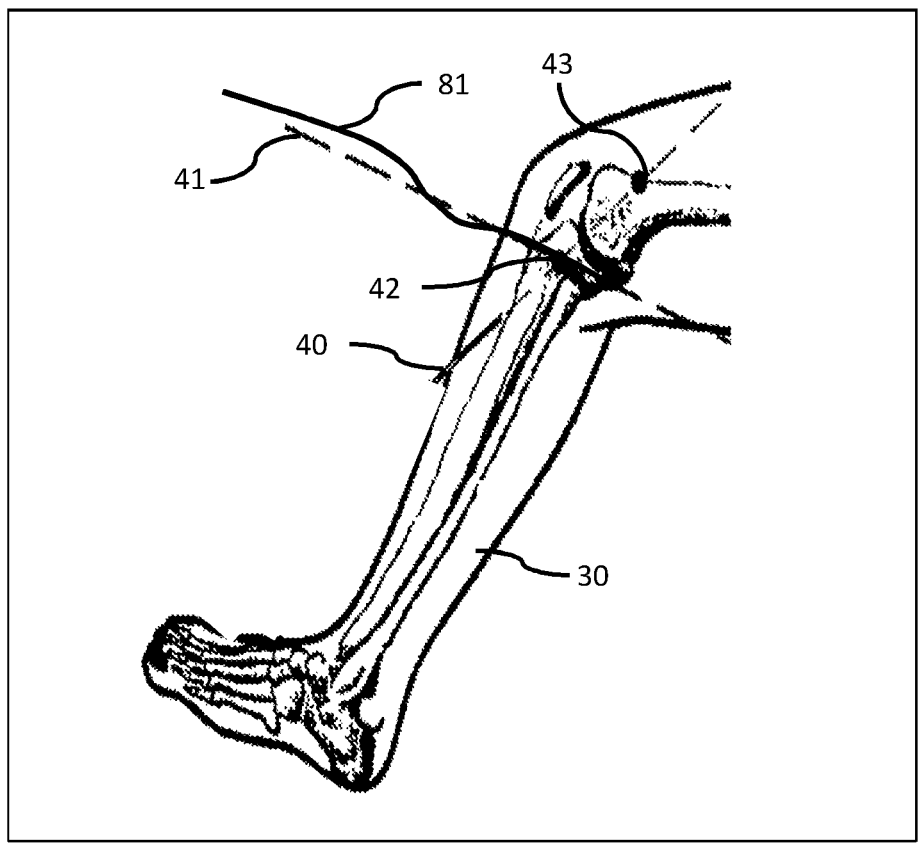
FIG. 9 is a schematic view of a display illustrating another embodiment of displaying the tracked position and orientation of the surgical object relative to the pre-operative plan.

FIGS. 8 and 9 illustrate embodiments of the pre-operative plan with the first path 40 and the second path 41 together with the data of the virtual structure 30. The data is rendered on a display that may be visible to the surgeon during surgery, and thus may included in the feedback device. The coordinate systems of the patient and the pre-operative plan have been aligned, and the position of the surgical object calibrated if needed. At least a portion of the data of the pre-operative plan, and in relation thereto, position and orientation information of the surgical object in the second coordinate system is displayed in the first coordinate system represented by a current position of the virtual object and based on the tracked position and orientation of the surgical object.

In the embodiment of FIG. 8, a virtual object in the form of a virtual surgical instrument 80 is shown in the display. The position and orientation of the virtual surgical instrument 80 relative to the virtual structure 30 in the first coordinate system, i.e. the coordinate system of the planning unit 1, corresponds to the position and orientation of the surgical instrument relative to the patient structure in the second coordinate system, i.e. the coordinate system in which the patient is present. In this embodiment, the feedback of the position and orientation of the surgical instrument in the second coordinate system is the display of the current position and orientation of the virtual surgical instrument 80. Hence, as the surgical instrument moves in the second coordinate system, the virtual surgical instrument 80 will move in real time in the first coordinate system relative to the virtual structure 30, which will be shown on the display. Hence, since the first path 40 and the second path 41 are also displayed, the surgeon can monitor in real time whether the surgical instrument is correctly positioned and oriented relative to its planned positions and orientations, and if not correct its position to follow the path. In this embodiment, the virtual surgical instrument 80 is shown in a first position relative the first path 40 and in a second position relative to the second path 41. This is for illustrative purposes on order to indicate different stages of the surgery. In other embodiments, however, multiple indications of movement of multiple virtual surgical instruments, possibly of different types, may be shown at the same time in the first coordinate system.

In the embodiment of FIG. 9, feedback of the tracked positions and orientations of the surgical object in the second coordinate system is indicated as a trace 81 in the first coordinate system. As is illustrated therein, before the surgical object has reached the entry position 42, it deviates quit significantly from the planned path 41. However, since the planned path 41 extends before the entry point, the surgeon is guided towards the planned path 41 and is able to follow the planned path 41 between the entry position 42 and the end position 43. The trace 81 may be displayed in a different colour than the planned positions and orientations represented by the paths 40, 41. Furthermore, a warning indication may be displayed as feedback if the position of the surgical object deviates more than an allowed amount from the planned positions and orientations. The allowed amount may be predetermined such as fixed, system dependent, depending on type of surgical procedure, etc., or set during planning. The warning may e.g. be a visible warning, such as the trace 81 may shift colour from red to green when within the allowed rang or shape to bolder when outside allowed range. Additionally or alternatively, the warning may be acoustic, such as an alarm. The warning indication may in other embodiments be provided separate from other embodiments of the invention as described herein. In the context of the invention, it provides for a more robust and reliable surgical navigation system.

For an implant procedure, the feedback may be used to verify a correct position and orientation of the implant relative to the patient structure. For example, the position of the implant may be registered as discussed above, using the position of a surface thereof that can be captured using a position registration unit, such as a position registration probe, for example a tracked probe. Then, actual position of the implant relative to the patient structure can be compared to the planned position and orientation of the virtual representation thereof relative to the virtual structure representing the patient structure. The implant may e.g. comprise one or several landmarks that are known to be visible after implantation of the implant and yet having being arranged in known pre-determined positions on the implant. This may speed up registration of the position and orientation of the implant, since registration process for a captured point cloud thereof is relatively computational simple. This can for example be used for checking position and orientation of a femur component relative to a femur, and acetebular cup relative to an acetabulum.

Calibration

Figure 10A:
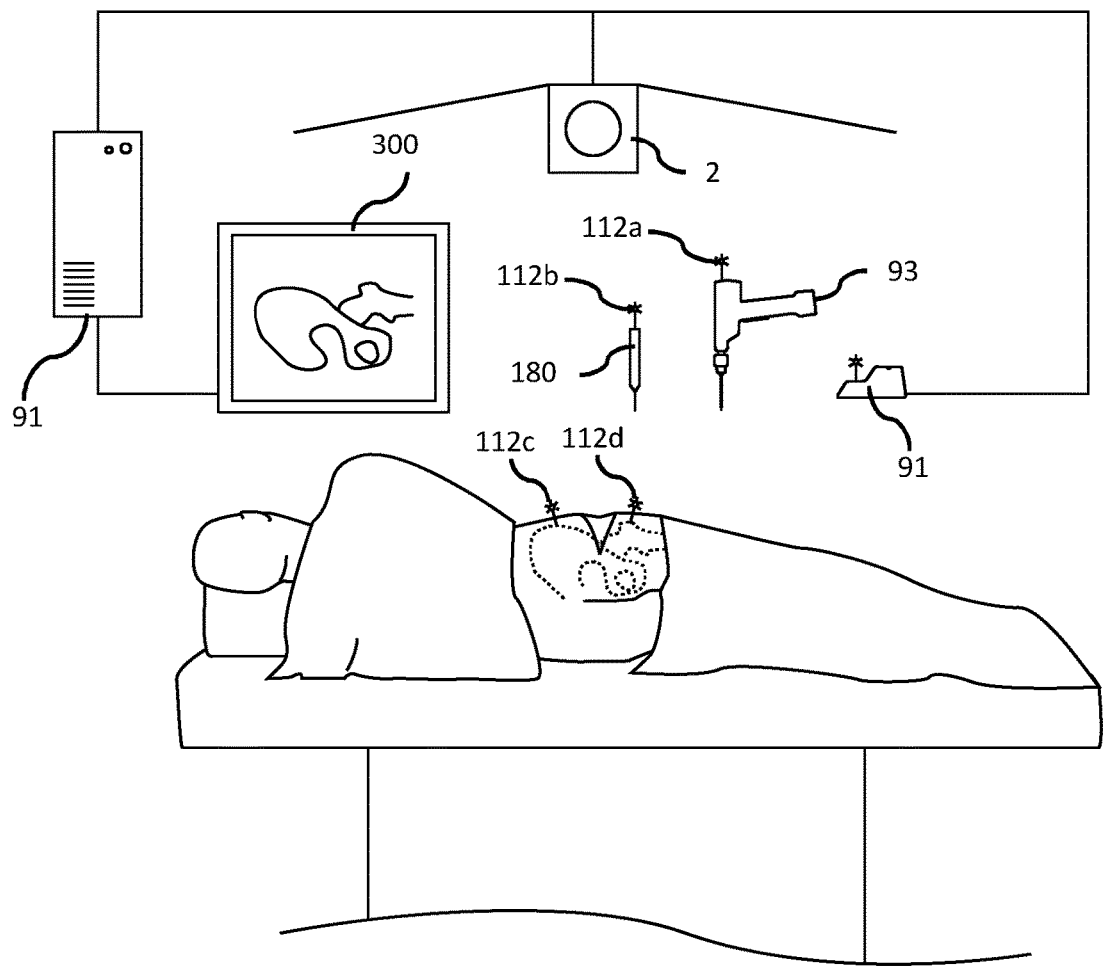
FIGS. 10a-10c are perspective views of the system according to embodiments of the invention.
Figure 10B:
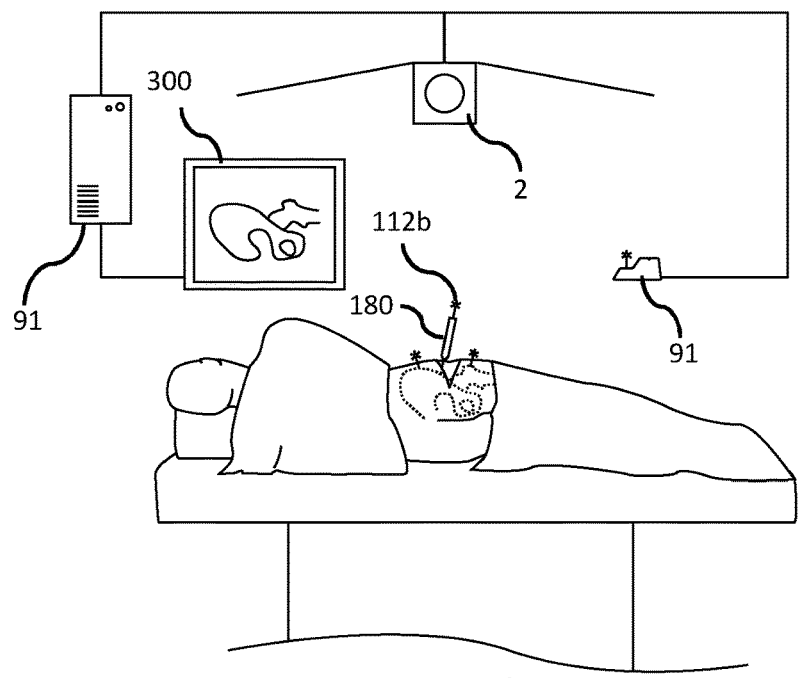
Figure 10C:
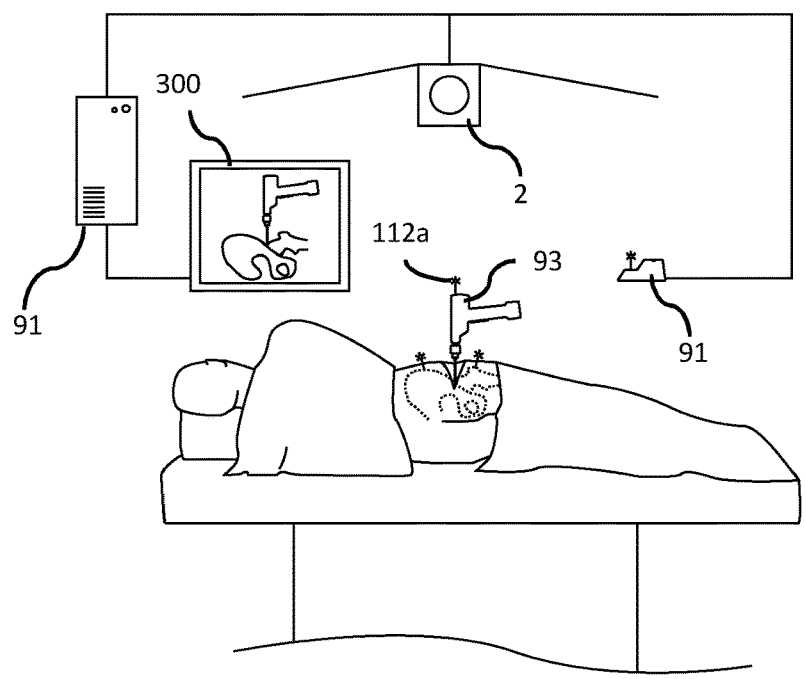

FIGS. 10a-10c illustrate embodiments of a surgical navigation system comprising a calibration unit 91. The calibration unit 91 may be a position calibration unit 91 adapted to calibrate the position of any navigation unit within the surgical navigation system. As discussed above, calibrating the navigation unit allows for calibrating the position of the surgical object 93, such as an end-effector 94 thereof, and/or a position registration unit 180, such as the position registration probe, thereof. The surgical navigation system is provided within the surgical theatre or operating room. Furthermore, the surgical navigation system may be adapted to track the position of navigation unit, and thus the surgical object and/or position registration unit, such as illustrated in FIG. 10c. The calibration unit 91 may be associated with and/or comprise the second coordinate system, which may be referenced to the first coordinate system. Alternatively or additionally, the calibration unit 91 may have a fixed position within the surgical navigation system and thus within the second coordinate system, such as described above. The calibration unit 91 has a fixed position within the second coordinate system when it is used for calibrating the position of various objects, as will be described below.

In some embodiments, the calibration unit 91 is provided as a docketing station. The origin of the second coordinate system may be provided within the calibration unit. Alternatively or additionally, the position of the calibration unit 91 within the second coordinate system may be registered. The calibration unit 91 is adapted to calibrate the position of at least one of the surgical object 93, the navigation unit thereof 112a, a detachable navigation unit as discussed above, other tools, as will be described below, and/or the position registration unit, within the surgical navigation system, such as within the second coordinate system. In more detail, each object to track may comprise a navigation unit 112a. Before the surgery commences, the position of the navigation unit 112a may be calibrated, i.e. its position and/or orientation within the operating room may be registered. Thus, the position and orientation of the navigation unit 112a relative to the surgical object may be determined and tracked, i.e. dynamically referenced. For example, the position and orientation of the navigation unit 112a may have a fixed position and orientation relative an end effector of the surgical object and/or the position registration probe of the position registration unit. After calibration of the position and/or orientation of the navigation unit 112a is made, the position and orientation of the navigation unit 112a, and hence the position and orientation of the surgical object and/or position registration unit, may be tracked in space as will be discussed in more detail below.

Once the position of the navigation unit 112a within the navigation system has been calibrated, the position of the navigation unit 112a within the second coordinate system may be tracked and its position or the position of the surgical object translated into a position within the first coordinate system.

Similarly, the position registration unit 180 may comprise the navigation unit 112b. The position registration unit 180 may comprise a sensor, such as the position registration probe. The position registration probe may activate the navigation unit 112b of the position registration unit 180, whereby positions from the surface of the patient structure may be obtained. The position registration probe may e.g. by a touch sensitive probe, whereby a tip thereof activates the navigation unit 112b, such that its position is determined while the tip touches a surface, such as a surface of the surgical structure. Alternative, the position registration unit 180 may comprise an actuator, such as a button, to activate the navigation unit 112b thereof. Thus, a point cloud may generated, such as described above and may be used to register the patient structure to the virtual structure. The registered information about the patient structure is registered to the virtual structure. Furthermore, the registered surface data may be presented aligned with the virtual structure by the output device, such as the display 10. Hence, any deviation between a virtual structure obtained from the plan data and a virtual structure obtained from the registered surface data may be indicated on the feedback device.

In some embodiments, such as illustrated in the embodiment of FIG. 10a, at least one patient structure navigation unit 112c, 112d is attached to the patient structure during the surgical procedure. The patient structure navigation unit 112c, 112d may be attached to a pin or rod or any other device proving a relatively fixed position for the navigation unit and that may be attached to a bony anatomy of the patient that has a fixed relationship to the patent structure subject to the surgery. While obtaining the positions from the surface of the patient structure, the position of the navigation unit 112c, 112d attached to the patient structure within the second coordinate system is also registered. Hence, each point of the point cloud representing the surface of the patient structure may be related to the patient structure navigation unit 112c, 112d. During surgery, the position of the patient structure navigation unit 112c, 112d may be tracked whereby the position of the patient structure is also tracked, i.e. dynamically referenced, since there is a fixed relationship there between. This has the benefit that the surface of the patient structure does not have to be in the line of sight of a position receiver of the surgical navigation system. Furthermore, if the exposed surface during surgery comprises relatively little bony surfaces and more cantilever surfaces and the patient data has been obtained using CT, the system becomes more robust and reliable, since a optical system, such as a camera, for tracking a surface captures the cantilever surfaces. CT has one resolution where cantilever is not captured, whereas the optical system has a different resolution where cantilever is captured, wherein the registration and referencing of the patient structure is inaccurate. According to embodiments of the invention, very little bony anatomy may be captured at the same time as the patient structure navigation unit, wherein the accuracy and robustness of the system is superior.

Figure 11A:
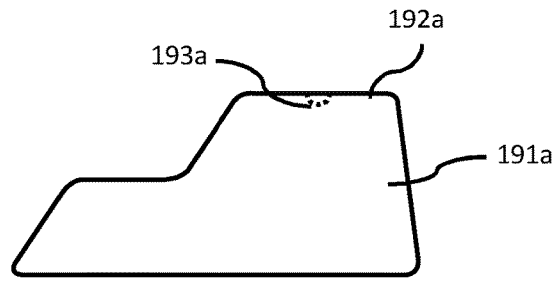
FIGS. 11a-11e are front views of embodiments of calibration units.
Figure 11B:
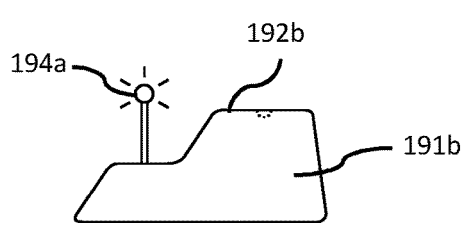
Figure 11C:
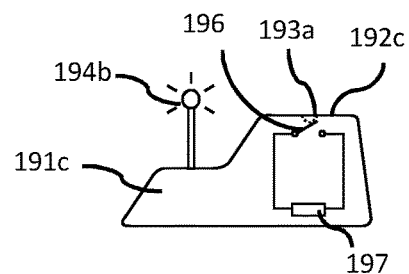

FIGS. 11a-11e illustrates embodiments of the calibration unit. In these embodiments, the calibration unit 191 comprises a base unit 192a, 192b, 192c for positioning the calibration unit 191 at an arbitrarily position within the surgical navigation system. The calibration unit, such as at the base unit 192a, 192b, 192c, comprises an external surface for receiving a surface of the surgical object 93, such as a surface of a surgical instrument, for example an end-effector thereof. The external surface of the calibration unit 191 may have a predetermined shape, such as may comprise a recess or protrusion 193a, 193b, illustrated in phantom lines in FIGS. 11a-11e. The surface with a predetermined shape may be symmetrical, such as half-spherical or dome shaped. Alternatively, the surface with a predetermined shape is asymmetrical. In the embodiment of FIGS. 11b-11c, the calibration unit 191b, 191c comprises a navigation unit 194a, 194b. The position of the external surface for receiving the surface of the surgical object relative the navigation unit 194a, 194b of the calibration unit 191 may be fixed and known. Hence, the position of the external surface for receiving the surface of the surgical object within the second coordinate system is known or may be determined by registering the position of the navigation unit 194a, 194b of the calibration unit.

In the embodiment of FIG. 11c, the base unit comprises an actuator 196, such as a switch, for initiating the registration process for registering the position of the end-effector. The actuator 196 may be located at the external surface for receiving the surface of the surgical object, such as within the recess or at the protrusion. When the end-effector is positioned at the external surface it may activate the actuator 196, such as closing the switch, to initiate the registration process. When the end-effector is removed from the actuator, the registration process is ended.

Figure 11D:
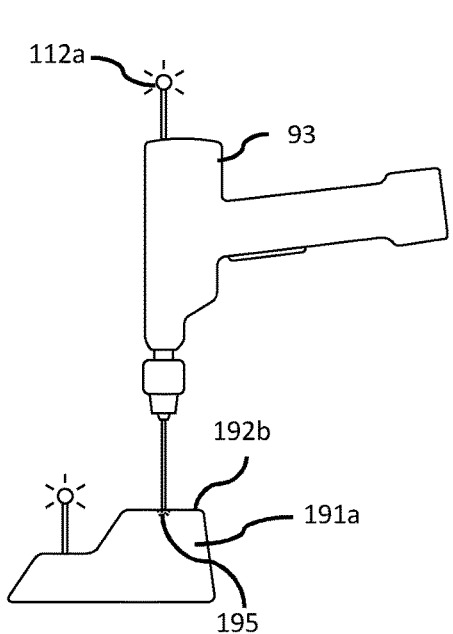
Figure 11E:
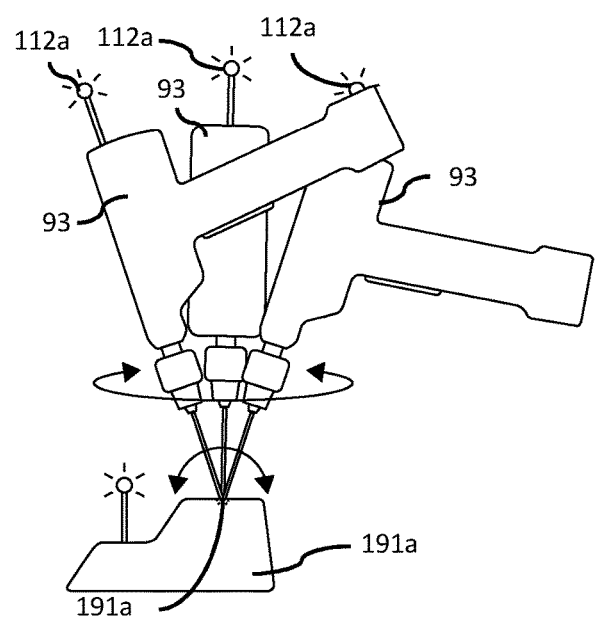

FIGS. 11d-11e illustrate an embodiment for registering a position of the surgical object 93 or the position registration unit in the second coordinate system. The surgical object 93 may comprise the end-effector 195, such as the tip of an instrument or tool, and the position registration unit may comprise the position registration probe. To calibrate the position in the second coordinate system, the end-effector 195 is positioned at the recess or protrusion, such as within the recess or over the protrusion, such that it has a substantially fixed position at one point and/or in one plane, e.g. the x-z plane, illustrated in FIG. 11d. The surgical object 93 also comprises navigation unit 112a, such as described above. Then, as is illustrated in FIG. 11e, the position of the end-effector 195, and optionally an longitudinal axis relative the end-effector, such as of the instrument or tool, may be registered while moving the surgical object 93 in at least a second plane, such as the x-y plane and/or y-z plane, and while the end-effector 195 is positioned at the external surface, i.e. has a relatively fixed position in one point or one plane, such as the x-z plane, and at the same time multiple positions of the navigation unit is registered. The registered positions of the navigation unit 112a forms a shape, such as a dome shape, having an origin located at the position of the end-effector 195 and with a radius determined by the distance between the origin and the registered positions. Hence, the registered positions of the navigation unit 112a may be used to determine the position of the end-effector 195 and the longitudinal axis of the instrument or tool. In FIG. 11e, the surgical object 93 is shown in multiple positions for illustrative purposes.

In some embodiments, the position of the end-effector relative to the navigation unit of the object carrying the end-effector is known. In such an embodiment, the position of the navigation unit is calibrated by the positioning the end-effector in the recess or protrusion and registering the positions of the navigation unit of the moveable device, such as the surgical object or position registration unit, and the position of the navigation unit of the calibration unit. The position of the recess or protrusion relative the navigation unit of the calibration unit is known, wherein the position as well as the orientation of the end-effector may be determined based on the known position of the end-effector relative the navigation unit carried by the moveable object and the registered position of its navigation unit and the registered position of the calibration unit.

The actuator may be connected to a communication unit 197, which in turn is connected to the communication hub 4. Furthermore, the communication hub 4 may be connected to the position registration unit. Hence, the position registration unit and associated processes for determining the positions of the various devices of the system may be initiated by closing a circuit connected to the actuator 197. The calibration unit 191 may be connected to the communication hub using a wired or wireless connection, such as a WiFi or Bluetooth® communication unit.

Figure 12:
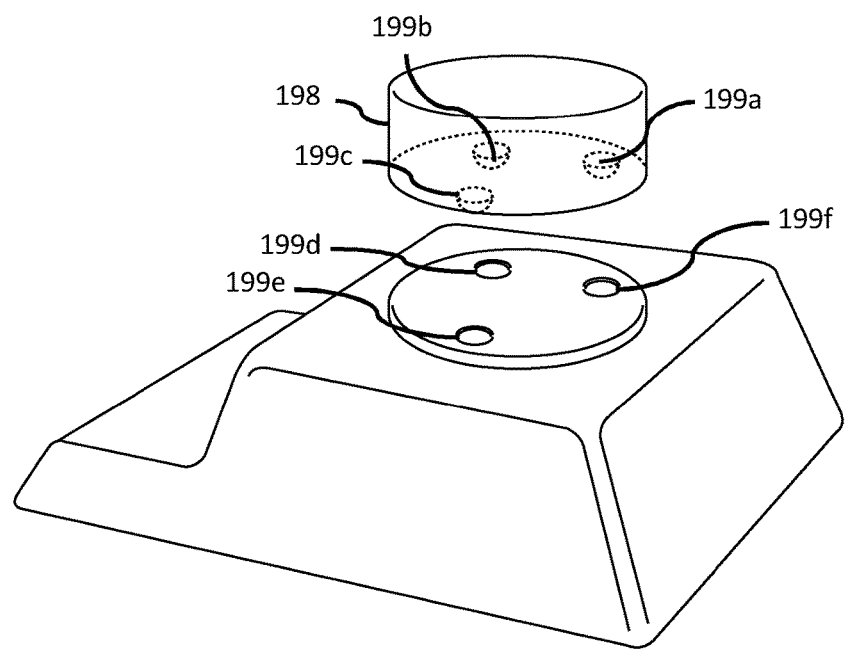
FIG. 12 is a perspective view of an embodiment of a calibration unit.

FIG. 12 illustrates a detachable navigation unit 198. The detachable navigation unit 198 comprises a surface that can be positioned at the base unit in a fixed positional relationship. The connection interface there between may have a shape such the detachable navigation unit 198 has a fixed positional and orientational relationship to the calibration unit. This may be achieved using one or more protrusions (illustrated in phantom in FIG. 12) 199a, 199b, 199c and recesses 199d, 199e, 199f having complementary shapes. A corresponding connection interface may be integrated with the object to carry the navigation unit, such as the surgical object or the position registration unit. The position of the detachable navigation unit 198 may be calibrated by registering its position relative the connection interface of the calibration unit, such as utilizing any of registration technique described above relative FIGS. 11a-11d. Once the position of the detachable navigation unit 198 is determined, it may be connected to the object to carry. The type of object that fits to the detachable navigation unit 198 may be predetermined, such as programmed within a memory of the detachable navigation unit 198, or defined utilizing the input device. Furthermore, the position of the end-effector relative to the detachable navigation unit 198 may be known. This may also be used with a navigation unit integrated with the object. Hence, the position of the end-effector may be tracked when the detachable navigation unit 198 is attached to the object to carrying it.

As is illustrated in FIGS. 10a-10c, the surgical navigation system may be adapted to track the position of multiple objects. The surgical navigation system comprises the calibration unit 91, such as described in the embodiments of FIGS. 11a-11d and 12, respectively. The position of a surgical object 93 in the form a surgical instrument may be calibrated and tracked, such as described above. Another surgical object is a position registration unit 180. Furthermore, another device is the patient structure navigation unit 112c, 112d attachable to the patient structure. In this embodiment one patient structure navigation unit 112d is attached to the femur and another patient structure navigation unit 112c to the pelvis. Hence, if the patient moves after registration of the positional information of the surface of the patient structure together with its patient structure navigation unit 112c, 112d, the position of the patient structure is tracked. The surgical navigation system also comprises a feedback unit, such as a display 300. The patient structure may be aligned with the virtual structure, such as described above. Utilizing the components of the surgical navigation system, the position of the surgical object relative to the pre-operative plan and the patient structure may be tracked in real-time, such as illustrated in FIG. 11c, wherein the position of the virtual object is displayed in relation to the virtual structure in the same relationship as the surgical object 93 to the patient structure. Furthermore, by calibrating the navigation unit 112a of the surgical object, and thus the position of the end-effector, the accuracy, robustness, and reliability, and flexibility of the system is enhanced compared to an uncalibrated system or a system wherein the calibration is based on scanning the surgical object and registering against CAD objects.

The calibration unit provides for tracking a standard surgical object of arbitrary shape, to which a position sensor is attached at any position thereof. By registering the position of the navigation unit of the surgical object at a known position of a calibration unit, the position of the end-effector may be determined. Hence, the position of the end-effector is calibrated against at least one known position of the calibration unit. The position may be calibrated by calculating the position, such as described above in relation to the embodiments of FIGS. 11a-11d, or it may be predetermined, such as described relative to the embodiments of FIG. 1. Hence, the system according to the invention may be integrated with any surgical object, such as surgical tools and instrument, that are on the marked and no special purpose instruments and tools may be acquired. Hence, the system is very flexible and can be implemented at a low cost. Furthermore, calibration of the components of the system is flexible and efficient.

The processes and systems described herein may be performed on or encompass various types of hardware, such as computer systems. In some embodiments, computer, display, and/or input device, may each be separate computer systems, applications, or processes or may run as part of the same computer systems, applications, or processes—or one of more may be combined to run as part of one application or process—and/or each or one or more may be part of or run on a computer system. A computer system may include a bus or other communication mechanism for communicating information, and a processor coupled with the bus for processing information. The computer systems may have a main memory, such as a random access memory or other dynamic storage device, coupled to the bus. The main memory may be used to store instructions and temporary variables. The computer systems may also include a read-only memory or other static storage device coupled to the bus for storing static information and instructions. The computer systems may also be coupled to a display, such as a CRT or LCD monitor. Input devices may also be coupled to the computer system. These input devices may include a mouse, a trackball, or cursor direction keys.

Each computer system may be implemented using one or more physical computers or computer systems or portions thereof. The instructions executed by the computer system may also be read in from a computer-readable medium. The computer-readable medium may be a CD, DVD, optical or magnetic disk, laserdisc, carrier wave, or any other medium that is readable by the computer system. In some embodiments, hardwired circuitry may be used in place of or in combination with software instructions executed by the processor. Communication among modules, systems, devices, and elements may be over a direct or a switched connection, and wired or wireless networks or connections, via directly connected wires, or any other appropriate communication mechanism. The communication among modules, systems, devices, and elements may include handshaking, notifications, coordination, encapsulation, encryption, headers, such as routing or error detecting headers, or any other appropriate communication protocol or attribute. Communication may also messages related to HTTP, HTTPS, FTP, TCP, IP, ebMS OASIS/ebXML, secure sockets, VPN, encrypted or unencrypted pipes, MIME, SMTP, MIME Multipart/Related Content-type, SQL, etc.

Any appropriate 3D graphics processing may be used for displaying or rendering including processing based on OpenGL, Direct3D, Java 3D, etc. Whole, partial, or modified 3D graphics packages may also be used, such packages including 3DS Max, SolidWorks, Maya, Form Z, Cybermotion 3D, or any others. In some embodiments, various parts of the needed rendering may occur on traditional or specialized graphics hardware. The rendering may also occur on the general CPU, on programmable hardware, on a separate processor, be distributed over multiple processors, over multiple dedicated graphics cards, or using any other appropriate combination of hardware or technique.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A method for computer assisted orthopedic feedback of at least one surgical instrument relative a pre-operative plan, wherein the surgical instrument is moveable relative to a patient structure during surgery; the pre-operative plan including a virtual structure, which is a virtual representation of the patient structure; comprising:
   providing the pre-operative plan including planned position and orientation of an implant relative to the virtual structure;
   obtaining a position of the patient structure using a surgical navigation system;
   obtaining a position of at least one surgical instrument using the surgical navigation system;
   registering the patient structure to the virtual structure;
   tracking a current position and orientation of the at least one surgical instrument relative said patient structure using the surgical navigation system; and
   providing feedback of the current position and orientation of the at least one surgical instrument relative to the planned position and orientation of the implant based on the tracked current position and orientation of the at least one surgical instrument.

2. The method according to claim 1, wherein obtaining the position of the at least one surgical instrument comprises calibrating at least one position of the surgical instrument relative a calibration unit within the surgical navigation system.

3. The method according to claim 2, further comprising calibrating an end-effector of the surgical instrument relative the calibration unit.

4. The method according to claim 2, wherein calibrating the at least one position of the surgical object comprises calibrating a position of a navigation unit at the surgical instrument relative a surface of the calibration unit, said surface having a predetermined position at the calibration unit.

5. The method according to claim 4, wherein calibrating the position of the navigation unit at the surgical instrument comprises:
   determining a position of a navigation unit at the calibration unit, the navigation unit at the calibration unit having a fixed positional relationship relative the surface having the predetermined position.

6. The method according to claim 4, wherein calibrating the position of the navigation unit at the surgical instrument comprises:
   registering multiple positions of the navigation unit at the surgical instrument while it is moved and a position of an end-effector of the surgical instrument is substantially fixed at the surface having the predetermined position, and
   determining the position of the end-effector based on the registered multiple positions of the navigation unit at the surgical instrument.

7. The method according to claim 1, wherein providing the feedback comprises providing at least one of:
   visual feedback of a current position and orientation of the surgical instrument relative to the planned orientation and position of the implant on a display in response to the tracked current position and orientation of the surgical instrument;
   visual indication of a deviation of a current position and orientation of the surgical instrument relative the planned position and orientation of the implant on a display in response to the tracked current position and orientation of the surgical implant; and
   visual indication of the deviation of the current position and orientation of the surgical instrument relative the planned position and orientation of the implant in response to the tracked current position and orientation of the surgical instrument, wherein the visual indication is indicated at the surgical instrument.

8. The method according to claim 1, wherein tracking the current position and orientation of the patient structure comprises tracking a position of a navigation unit, which is attached to the patient structure, using the surgical navigation system.

9. The method according to claim 1, further comprising obtaining a position of at least one implant for implantation into the patient structure.

10. The method according to claim 1, wherein obtaining the position of the patient structure comprises obtaining a position and orientation of a bony anatomy of the patient.

11. The method according to claim 1, wherein providing the pre-operative plan comprises:
   accessing volumetric scan data, wherein the scan data comprises patient structure scan data;
   converting the patient structure scan data into the virtual structure, which comprises a three dimensional representation of the patient structure;
   planning at least one position and orientation of the implant relative to the virtual structure; and
   including at least one of the scan data and the three dimensional representation of the virtual structure together with the planned position and orientation of the implant in the pre-operative plan.

12. The method according to claim 1, further comprising attaching a tracking unit, which is detachable and attachable, to the surgical instrument; and
  calibrating at least one position of the surgical instrument relative a calibration unit within the surgical navigation system.

13. The method according to claim 12, further comprising attaching a tracking unit, which is detachable and attachable, to the calibration unit prior to calibrating said at least one position of the surgical instrument relative the calibration unit.

14. The method according to claim 13, further comprising calibrating at least one position of the calibration unit within the surgical navigation system after attaching the tracking unit to said calibration unit.

15. The method according to claim 12, wherein attaching said tracking unit to said surgical instrument comprises mating a connection interface, which has at least one projection or recess, with a connection interface at the surgical instrument, said connection interface at said surgical instrument having a shape that is complementary to a shape of the connection interface of the navigation unit.

16. The method according to claim 15, wherein attaching said tracking unit comprises mating the connection interface, which has multiple projections or recesses, with the connection interface at the surgical instrument.

* * * * *